(12) United States Patent
Hunter

(10) Patent No.: US 8,187,893 B2
(45) Date of Patent: May 29, 2012

(54) MASS SPECTROMETRIC BASED ASSAY FOR PRESENCE OF A PROTEIN WITHOUT THE USE OF A STANDARD

(75) Inventor: Christie L. Hunter, San Mateo, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 7 days.

(21) Appl. No.: 12/572,042

(22) Filed: Oct. 1, 2009

(65) Prior Publication Data

US 2010/0233815 A1 Sep. 16, 2010

Related U.S. Application Data

(63) Continuation of application No. 11/580,221, filed on Oct. 12, 2006, now abandoned.

(60) Provisional application No. 60/727,187, filed on Oct. 13, 2005.

(51) Int. Cl.
*G01N 24/00* (2006.01)

(52) U.S. Cl. .......................... 436/173; 436/86

(58) Field of Classification Search .................. None
See application file for complete search history.

(56) References Cited

U.S. PATENT DOCUMENTS

| | | | |
|---|---|---|---|
| 4,121,121 A | 10/1978 | Gabeier |
| 4,361,812 A | 11/1982 | Farrell et al. |
| 5,209,919 A | 5/1993 | Turteltaub et al. |
| 5,668,708 A | 9/1997 | Scapellati |
| 6,329,146 B1 | 12/2001 | Crooke et al. |
| 6,387,629 B1 | 5/2002 | Schneider et al. |
| 6,391,649 B1 | 5/2002 | Chait et al. |
| 6,461,829 B1 | 10/2002 | Kahne |
| 6,465,259 B1 | 10/2002 | Janssen et al. |
| 6,629,040 B1 | 9/2003 | Goodlett et al. |
| 6,642,059 B2 | 11/2003 | Chait et al. |
| 6,653,076 B1 | 11/2003 | Franza, Jr. et al. |
| 6,656,690 B2 | 12/2003 | Crooke et al. |
| 6,670,194 B1 | 12/2003 | Aebersold et al. |
| 6,770,486 B1 | 8/2004 | Griffey et al. |
| 6,824,981 B2 | 11/2004 | Chait et al. |
| 6,858,839 B1 | 2/2005 | Anderson et al. |
| 6,864,089 B2 | 3/2005 | Figeys et al. |
| 6,864,099 B2 | 3/2005 | Regnier |
| 6,872,575 B2 | 3/2005 | Regnier |
| 6,969,614 B1 | 11/2005 | Liotta et al. |
| 6,982,414 B2 | 1/2006 | Bateman et al. |
| 7,045,296 B2 | 5/2006 | Parker et al. |
| 7,070,949 B2 | 7/2006 | Suckau et al. |

OTHER PUBLICATIONS

Hopp, et al., Proc. Natl. Mad. Sci., 78:3824.8, 1981.
Krokhin, et al., Mot Cell Proteomics, 3:908-19, 2004.
Adkins, et al., Mol. Cell. Proteomics, 1:947-55, 2002.
Craig, et al., J. Proteome Res., 3:1234-42, 2004.
Gerber, et al., Proc. Natl. Acad. Sci, 100(12):6940-6945, 2003.
Kuhn, et al., Proteomics, 4:1175-1186, 2004.
Covey, et al., Anal. Chem., 63(13):1193-1200.

(Continued)

*Primary Examiner* — Yelena G Gakh
(74) *Attorney, Agent, or Firm* — Ropes & Gray LLP

(57) ABSTRACT

The present teachings provide methods for the development of a mass spectrometric based assay for a protein in a sample using parent-daughter ion transition monitoring (PDITM). In various aspects, the present teachings provide methods for developing a mass spectrometric based assay for a protein in a sample without the use of a standard for the protein. In various embodiments, the sample comprises proteolytic fragments of a protein which is present in low abundance in the physiological fluid from which it is derived.

18 Claims, 19 Drawing Sheets

OTHER PUBLICATIONS

International Search Report, PCT/US2006/040263, mailed on Aug. 13, 2007.

Lenz, et al., "Validation of Identification of low abundance proteins using the MIDAS workflow on a 4000 Q TRAP LC/MS/MS system." Applied Biosystems. Technical Note-Internet Articel, 2005. URL: http://docs.appliedbiosystems.com/cms/groups/psm_marketing/documents/generaldocuments/cms_042563.pdf>.

Urlaub, et al., 53rd ASMS Conference on Mass Spectrometry and Allied Topics—Poster WP25-479, 2005.

Unwin, et al., Mol. Cell Proteomics, 4(8)1134-1144, 2005.

Cox, et al., J. of Biomol, Techniques: JBT, 16(2)83-90, 2005.

Anderson, et al., Mol. Cell Proteomics, 5(4):573-588, 2006.

Written Opinion of International Searching Authority, PCT/US2006/040263, mailed on Aug. 13, 2007.

Anderson, et al., J. of Proteome Res., 3:235-244, 2004.

Champion, et al., "Targeted Hypothesis-Driven Mass Spectrometry: MRM Initiated Detection and Sequencing using the MIDAS workflow for Faster, More Intelligent and Sensitive Protein Discovery and Characterization", Applied Biosystems, 2008.

Jacobs, et al., J. of Proteome Res., 4:1073-1085, 2005.

LaBaer, J. of Proteome Res., 4:1053-1059, 2005.

210

MGRKKIQITRIMDERNRQVTFTKRKFGLMKKAYELS
VLCDCEIAIIFNSSNKLFQYASTDMDKVLLKYTEYN
EPHESRTNSDIVEALNKKEHRGCDSPDPDTSYVLT
PHTEEKYKKINEEFDNMMRNHKIAPGLPPQNFSMS
VTVPVTSPNALSYTNPGSSLVSPSLAASSTLTDSSM
LSPPQTTLHRNVSPGAPQRPPSTGNAGGMLSTTD
LTVPNGAGSSPVGNGFVNSRASPNLIGATGANSLG
KVMPTKSPPPPGGGNLGMNSRKPDLRVVIPPSSK
GMMPPLSEEEELELNTQRISSSQATQPLATPVVSV
TTPSLPPQGLVYSAMPTAYNTDYSLTSADLSALQG
FNSPGMLSLGQVSAWQQHHLGQAALSSLVAGGQL
SQGSNLSINTNQNISIKSEPISPPRDRMTPSGFQQQ
QQQQQQQQPPPPPQPQPQPQPQPRQEMGRSP
VDSLSSSSSYDGSDREDPRGDFHSP
IVLGRPPNTEDRESPSPVKRMRMDAWVT

220

| Q1 | Q3 | SEQUENCE |
|---|---|---|
| 537.3 | 488.3 | NRQVTFTK |
| 545.2 | 496.2 | MRMDAWVT |
| 571.8 | 522.8 | NFIAVSAANR |
| 617.3 | 588.3 | SEPISPPRDR |
| 635.8 | 586.8 | KNFIAVSAANR |
| 642.3 | 593.3 | TNSDIVEALNK |
| 651.8 | 602.8 | ISSSGALDDDDK |
| 677.8 | 628.8 | IQITRIMDER |
| 699.8 | 650.8 | LFQYASTDMDK |
| 706.3 | 657.3 | TNSDEVEALNKK |
| 709.4 | 660.4 | NFIAVSAANRFK |

SEQUENCE LISTING

```
<160> NUMBER OF SEQ ID NOS: 72

<210> SEQ ID NO 1
<211> LENGTH: 11
<212> TYPE: PRT
<213> ORGANISM: Artificial Sequence
<220> FEATURE:
<223> OTHER INFORMATION: Peptide of fibronectin

<400> SEQUENCE: 1

Asp Leu Gln Phe Val Glu Val Thr Asp Val Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Proteolytic peptide

<400> SEQUENCE: 2

Ala Glu Ile Glu Tyr Leu Glu Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Derived from Homo Sapiens

<400> SEQUENCE: 3

Asp Ala Asp Pro Asp Thr Phe Phe Ala Lys
1               5                   10

<210> SEQ ID NO 4
<211> LENGTH: 15
<212> TYPE: PRT
```

<213> ORGANISM: Artificial Sequence
<220> FEATURE:
<223> OTHER INFORMATION: Derived from Homo Sapiens

<400> SEQUENCE: 4

```
Asp Trp Gly Leu Ser Val Tyr Ala Asp Lys Pro Glu Thr Thr Lys
1               5                   10                  15
```

<210> SEQ ID NO 5
<211> LENGTH: 9
<212> TYPE: PRT
<213> ORGANISM: Artificial Sequence
<220> FEATURE:
<223> OTHER INFORMATION: Derived from Homo Sapiens

<400> SEQUENCE: 5

```
Glu Ile Gly Glu Leu Tyr Leu Pro Lys
1               5
```

<210> SEQ ID NO 6
<211> LENGTH: 10
<212> TYPE: PRT
<213> ORGANISM: Artificial Sequence
<220> FEATURE:
<223> OTHER INFORMATION: Derived from Homo Sapiens

<400> SEQUENCE: 6

```
Leu Glu Thr Pro Asp Phe Gln Leu Phe Lys
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Derived from Homo Sapiens

<400> SEQUENCE: 7

```
Leu Gly Asn Gln Glu Pro Gly Gly Gln Thr Ala Leu Lys
1               5                   10
```

<210> SEQ ID NO 8
<211> LENGTH: 16
<212> TYPE: PRT
<213> ORGANISM: Artificial Sequence
<220> FEATURE:
<223> OTHER INFORMATION: Derived from Homo Sapiens

<400> SEQUENCE: 8

```
Asp Thr Glu Glu Glu Asp Phe His Val Asp Gln Val Thr Thr Val Lys
1               5                   10                  15
```

<210> SEQ ID NO 9
<211> LENGTH: 18
<212> TYPE: PRT
<213> ORGANISM: Artificial Sequence
<220> FEATURE:
<223> OTHER INFORMATION: Derived from Homo Sapiens

<400> SEQUENCE: 9

```
Leu Leu Ile Tyr Ala Val Leu Pro Thr Gly Asp Val Ile Gly Asp Ser
1               5                   10                  15

Ala Lys
```

<210> SEQ ID NO 10
<211> LENGTH: 12
<212> TYPE: PRT

```
<213> ORGANISM: Artificial Sequence
<220> FEATURE:
<223> OTHER INFORMATION: Derived from Homo Sapiens

<400> SEQUENCE: 10

Ala Leu Gln Asp Gln Leu Val Leu Val Ala Ala Lys
1               5                   10

<210> SEQ ID NO 11
<211> LENGTH: 14
<212> TYPE: PRT
<213> ORGANISM: Artificial sequence
<220> FEATURE:
<223> OTHER INFORMATION: Derived from Homo Sapiens

<400> SEQUENCE: 11

Pro Lys Asp Pro Thr Phe Ile Pro Ala Pro Ile Gln Ala Lys
1               5                   10

<210> SEQ ID NO 12
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 12

Asp Asp Leu Tyr Val Ser Asp Ala Phe His Lys
1               5                   10

<210> SEQ ID NO 13
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 13

Ala Thr Glu His Leu Ser Thr Leu Ser Glu Lys
1               5                   10

<210> SEQ ID NO 14
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 14

Ser Pro Glu Leu Gln Ala Glu Ala Lys
1               5

<210> SEQ ID NO 15
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 15

Ser Leu Ala Pro Tyr Ala Gln Asp Thr Gln Glu Lys
1               5                   10

<210> SEQ ID NO 16
<211> LENGTH: 9
<212> TYPE: PRT
<213> ORGANISM: Artificial sequence
<220> FEATURE:
```

```
<223> OTHER INFORMATION: Derived from Homo Sapiens

<400> SEQUENCE: 16

Phe Pro Glu Val Asp Val Leu Thr Lys
1               5

<210> SEQ ID NO 17
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 17

Thr Glu Val Ile Pro Pro Leu Ile Glu Asn Arg
1               5                   10

<210> SEQ ID NO 18
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 18

Thr Pro Asp Val Ser Ser Ala Leu Asp Lys
1               5                   10

<210> SEQ ID NO 19
<211> LENGTH: 21
<212> TYPE: PRT
<213> ORGANISM: Artificial sequence
<220> FEATURE:
<223> OTHER INFORMATION: Derived from Homo Sapiens

<400> SEQUENCE: 19

Ser Thr Ala Ala Met Ser Thr Tyr Thr Gly Ile Phe Thr Asp Gln Val
1               5                   10                  15

Leu Ser Val Leu Lys
            20

<210> SEQ ID NO 20
<211> LENGTH: 16
<212> TYPE: PRT
<213> ORGANISM: Artificial sequence
<220> FEATURE:
<223> OTHER INFORMATION: Derived from Homo Sapiens

<400> SEQUENCE: 20

Asp Ala Leu Ser Ser Val Gln Glu Ser Gln Val Ala Gln Gln Ala Arg
1               5                   10                  15

<210> SEQ ID NO 21
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 21

Leu Gly Pro Leu Val Glu Gln Gly Arg
1               5

<210> SEQ ID NO 22
<211> LENGTH: 9
<212> TYPE: PRT
<213> ORGANISM: Artificial sequence
```

```
<220> FEATURE:
<223> OTHER INFORMATION: Derived from Homo Sapiens

<400> SEQUENCE: 22

Ala Thr Val Val Tyr Gln Gly Glu Arg
1               5

<210> SEQ ID NO 23
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 23

Glu His Ser Ser Leu Ala Phe Trp Lys
1               5

<210> SEQ ID NO 24
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 24

Leu Ser Leu Glu Ile Glu Gln Leu Glu Leu Gln Arg
1               5                   10

<210> SEQ ID NO 25
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 25

Glu Tyr Thr Asp Ala Ser Phe Thr Asn Arg
1               5                   10

<210> SEQ ID NO 26
<211> LENGTH: 17
<212> TYPE: PRT
<213> ORGANISM: Artificial sequence
<220> FEATURE:
<223> OTHER INFORMATION: Derived from Homo Sapiens

<400> SEQUENCE: 26

Leu Phe Asp Ser Asp Pro Ile Thr Val Thr Val Pro Val Glu Val Ser
1               5                   10                  15

Arg

<210> SEQ ID NO 27
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 27

Asp Pro Pro Ser Asp Leu Leu Leu Leu Lys
1               5                   10

<210> SEQ ID NO 28
<211> LENGTH: 9
<212> TYPE: PRT
<213> ORGANISM: Artificial sequence
```

```
<220> FEATURE:
<223> OTHER INFORMATION: Derived from Homo Sapiens

<400> SEQUENCE: 28

Val Val Gly Gly Leu Val Ala Leu Arg
1               5

<210> SEQ ID NO 29
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 29

Thr Gly Leu Gln Glu Val Glu Val Lys
1               5

<210> SEQ ID NO 30
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 30

Ile Thr Gln Val Leu His Phe Thr Lys
1               5

<210> SEQ ID NO 31
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 31

Val Gly Asp Thr Leu Asn Leu Asn Leu Arg
1               5                   10

<210> SEQ ID NO 32
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 32

Ala Ile Glu Asp Tyr Ile Asn Glu Phe Ser Val Arg
1               5                   10

<210> SEQ ID NO 33
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 33

Glu Glu Leu Leu Pro Ala Gln Asp Ile Lys
1               5                   10

<210> SEQ ID NO 34
<211> LENGTH: 13
<212> TYPE: PRT
<213> ORGANISM: Artificial sequence
<220> FEATURE:
<223> OTHER INFORMATION: Derived from Homo Sapiens
```

```
<400> SEQUENCE: 34

Ser Pro Asp Val Ile Asn Gly Ser Pro Ile Ser Gln Lys
1               5                   10

<210> SEQ ID NO 35
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 35

Thr Val Ile Gly Pro Asp Gly His Lys
1               5

<210> SEQ ID NO 36
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 36

Gly Ser Glu Ser Gly Ile Phe Thr Asn Thr Lys
1               5                   10

<210> SEQ ID NO 37
<211> LENGTH: 13
<212> TYPE: PRT
<213> ORGANISM: Artificial sequence
<220> FEATURE:
<223> OTHER INFORMATION: Derived from Homo Sapiens

<400> SEQUENCE: 37

Gln Gly Phe Gly Asn Val Ala Thr Asn Thr Asp Gly Lys
1               5                   10

<210> SEQ ID NO 38
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 38

Asp Thr Val Gln Ile His Asp Ile Thr Gly Lys
1               5                   10

<210> SEQ ID NO 39
<211> LENGTH: 17
<212> TYPE: PRT
<213> ORGANISM: Artificial sequence
<220> FEATURE:
<223> OTHER INFORMATION: Derived from Homo Sapiens

<400> SEQUENCE: 39

Val Thr Trp Ala Pro Pro Pro Ser Ile Asp Leu Thr Asn Phe Leu Val
1               5                   10                  15

Arg

<210> SEQ ID NO 40
<211> LENGTH: 8
<212> TYPE: PRT
<213> ORGANISM: Artificial sequence
<220> FEATURE:
<223> OTHER INFORMATION: Derived from Homo Sapiens
```

```
<400> SEQUENCE: 40

Thr Gly Ala Gln Glu Leu Leu Arg
1               5

<210> SEQ ID NO 41
<211> LENGTH: 9
<212> TYPE: PRT
<213> ORGANISM: Artificial sequence
<220> FEATURE:
<223> OTHER INFORMATION: Derived from Homo Sapiens

<400> SEQUENCE: 41

Val Gly Tyr Val Ser Gly Trp Gly Arg
1               5

<210> SEQ ID NO 42
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 42

Asn Phe Pro Ser Pro Val Asp Ala Ala Phe Arg
1               5                   10

<210> SEQ ID NO 43
<211> LENGTH: 9
<212> TYPE: PRT
<213> ORGANISM: Artificial
<220> FEATURE:
<223> OTHER INFORMATION: Derived from Homo Sapiens

<400> SEQUENCE: 43

Thr Leu Glu Ala Gln Leu Thr Pro Arg
1               5

<210> SEQ ID NO 44
<211> LENGTH: 14
<212> TYPE: PRT
<213> ORGANISM: Artificial sequence
<220> FEATURE:
<223> OTHER INFORMATION: Derived from Homo Sapiens

<400> SEQUENCE: 44

Asp Ser Pro Val Leu Ile Asp Phe Phe Glu Asp Thr Glu Arg
1               5                   10

<210> SEQ ID NO 45
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 45

Ala Ala Ile Ser Gly Glu Asn Ala Gly Leu Val Arg
1               5                   10

<210> SEQ ID NO 46
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 46
```

```
Ala Phe Ile Gln Leu Trp Ala Phe Asp Ala Val Lys
1               5                   10
```

<210> SEQ ID NO 47
<211> LENGTH: 11
<212> TYPE: PRT
<213> ORGANISM: Artificial sequence
<220> FEATURE:
<223> OTHER INFORMATION: Derived from Homo Sapiens

<400> SEQUENCE: 47

```
Thr Val Gly Ser Asp Thr Phe Tyr Ser Phe Lys
1               5                   10
```

<210> SEQ ID NO 48
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 48

```
Tyr Trp Gly Val Ala Ser Phe Leu Gln Lys
1               5                   10
```

<210> SEQ ID NO 49
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 49

```
Leu Ser Ser Pro Ala Val Ile Thr Asp Lys
1               5                   10
```

<210> SEQ ID NO 50
<211> LENGTH: 7
<212> TYPE: PRT
<213> ORGANISM: Artificial sequence
<220> FEATURE:
<223> OTHER INFORMATION: Derived from Homo Sapiens

<400> SEQUENCE: 50

```
Leu Phe Leu Glu Pro Thr Arg
1               5
```

<210> SEQ ID NO 51
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 51

```
Glu Thr Ala Ala Ser Leu Leu Gln Ala Gly Tyr Lys
1               5                   10
```

<210> SEQ ID NO 52
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 52

```
Leu Val Asn Glu Val Thr Glu Phe Ala Lys
```

<210> SEQ ID NO 53
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 53

Val Gly Glu Tyr Ser Leu Tyr Ile Gly Arg
1               5                   10

<210> SEQ ID NO 54
<211> LENGTH: 14
<212> TYPE: PRT
<213> ORGANISM: Artificial sequence
<220> FEATURE:
<223> OTHER INFORMATION: Derived from Homo Sapiens

<400> SEQUENCE: 54

Glu Asp Pro Gln Thr Phe Tyr Tyr Ala Val Ala Val Val Lys
1               5                   10

<210> SEQ ID NO 55
<211> LENGTH: 13
<212> TYPE: PRT
<213> ORGANISM: Artificial sequence
<220> FEATURE:
<223> OTHER INFORMATION: Derived from Homo Sapiens

<400> SEQUENCE: 55

Ala Ala Asp Asp Thr Trp Glu Pro Phe Ala Ser Gly Lys
1               5                   10

<210> SEQ ID NO 56
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 56

Thr His Leu Pro Glu Val Phe Leu Ser Lys
1               5                   10

<210> SEQ ID NO 57
<211> LENGTH: 8
<212> TYPE: PRT
<213> ORGANISM: Artificial sequence
<220> FEATURE:
<223> OTHER INFORMATION: Derived from Homo Sapiens

<400> SEQUENCE: 57

Trp Glu Leu Asp Leu Asp Ile Lys
1               5

<210> SEQ ID NO 58
<211> LENGTH: 15
<212> TYPE: PRT
<213> ORGANISM: Artificial sequence
<220> FEATURE:
<223> OTHER INFORMATION: Derived from Homo Sapiens

<400> SEQUENCE: 58

Asp Val Trp Gly Ile Glu Gly Pro Ile Asp Ala Ala Phe Thr Arg
1               5                   10                  15

<210> SEQ ID NO 59
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 59

```
Phe Glu Asp Gly Val Leu Asp Pro Asp Tyr Pro Arg
1               5                   10
```

<210> SEQ ID NO 60
<211> LENGTH: 16
<212> TYPE: PRT
<213> ORGANISM: Artificial sequence
<220> FEATURE:
<223> OTHER INFORMATION: Derived from Homo Sapiens

<400> SEQUENCE: 60

```
Glu Ile Pro Ala Trp Val Pro Phe Asp Pro Ala Ala Gln Ile Thr Lys
1               5                   10                  15
```

<210> SEQ ID NO 61
<211> LENGTH: 507
<212> TYPE: PRT
<213> ORGANISM: Artificial sequence
<220> FEATURE:
<223> OTHER INFORMATION: Derived from Homo Sapiens

<400> SEQUENCE: 61

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu His Arg Gly Cys
                85                  90                  95

Asp Ser Pro Asp Pro Asp Thr Ser Tyr Val Leu Thr Pro His Thr Glu
            100                 105                 110

Glu Lys Tyr Lys Lys Ile Asn Glu Glu Phe Asp Asn Met Met Arg Asn
        115                 120                 125

His Lys Ile Ala Pro Gly Leu Pro Pro Gln Asn Phe Ser Met Ser Val
    130                 135                 140

Thr Val Pro Val Thr Ser Pro Asn Ala Leu Ser Tyr Thr Asn Pro Gly
145                 150                 155                 160

Ser Ser Leu Val Ser Pro Ser Leu Ala Ala Ser Ser Thr Leu Thr Asp
                165                 170                 175

Ser Ser Met Leu Ser Pro Pro Gln Thr Thr Leu His Arg Asn Val Ser
            180                 185                 190

Pro Gly Ala Pro Gln Arg Pro Pro Ser Thr Gly Asn Ala Gly Gly Met
        195                 200                 205

Leu Ser Thr Thr Asp Leu Thr Val Pro Asn Gly Ala Gly Ser Ser Pro
    210                 215                 220

Val Gly Asn Gly Phe Val Asn Ser Arg Ala Ser Pro Asn Leu Ile Gly
225                 230                 235                 240
```

```
Ala Thr Gly Ala Asn Ser Leu Gly Lys Val Met Pro Thr Lys Ser Pro
                245                 250                 255

Pro Pro Pro Gly Gly Asn Leu Gly Met Asn Ser Arg Lys Pro Asp
            260                 265                 270

Leu Arg Val Val Ile Pro Ser Ser Lys Gly Met Pro Pro Leu
            275                 280                 285

Ser Glu Glu Glu Leu Glu Leu Asn Thr Gln Arg Ile Ser Ser Ser
290                 295                 300

Gln Ala Thr Gln Pro Leu Ala Thr Pro Val Val Ser Val Thr Thr Pro
305                 310                 315                 320

Ser Leu Pro Pro Gln Gly Leu Val Tyr Ser Ala Met Pro Thr Ala Tyr
                325                 330                 335

Asn Thr Asp Tyr Ser Leu Thr Ser Ala Asp Leu Ser Ala Leu Gln Gly
                340                 345                 350

Phe Asn Ser Pro Gly Met Leu Ser Leu Gly Gln Val Ser Ala Trp Gln
                355                 360                 365

Gln His His Leu Gly Gln Ala Ala Leu Ser Ser Leu Val Ala Gly Gly
            370                 375                 380

Gln Leu Ser Gln Gly Ser Asn Leu Ser Ile Asn Thr Asn Gln Asn Ile
385                 390                 395                 400

Ser Ile Lys Ser Glu Pro Ile Ser Pro Pro Arg Asp Arg Met Thr Pro
                405                 410                 415

Ser Gly Phe Gln Gln Gln Gln Gln Gln Gln Gln Gln Gln Pro Pro
                420                 425                 430

Pro Pro Pro Gln Pro Gln Pro Gln Pro Pro Gln Pro Gln Pro Arg Gln
            435                 440                 445

Glu Met Gly Arg Ser Pro Val Asp Ser Leu Ser Ser Ser Ser Ser
            450                 455                 460

Tyr Asp Gly Ser Asp Arg Glu Asp Pro Arg Gly Asp Phe His Ser Pro
465                 470                 475                 480

Ile Val Leu Gly Arg Pro Pro Asn Thr Glu Asp Arg Glu Ser Pro Ser
                485                 490                 495

Val Lys Arg Met Arg Met Asp Ala Trp Val Thr
                500                 505

<210> SEQ ID NO 62
<211> LENGTH: 8
<212> TYPE: PRT
<213> ORGANISM: Artificial sequence
<220> FEATURE:
<223> OTHER INFORMATION: Derived from Homo Sapiens

<400> SEQUENCE: 62

Asn Arg Gln Val Thr Phe Thr Lys
1               5

<210> SEQ ID NO 63
<211> LENGTH: 8
<212> TYPE: PRT
<213> ORGANISM: Artificial
<220> FEATURE:
<223> OTHER INFORMATION: Derived from Homo Sapiens

<400> SEQUENCE: 63

Met Arg Met Asp Ala Trp Val Thr
1               5

<210> SEQ ID NO 64
```

```
<211> LENGTH: 10
<212> TYPE: PRT
<213> ORGANISM: Artificial
<220> FEATURE:
<223> OTHER INFORMATION: Derived from Homo Sapiens

<400> SEQUENCE: 64

Asn Phe Ile Ala Val Ser Ala Ala Asn Arg
1               5                   10

<210> SEQ ID NO 65
<211> LENGTH: 10
<212> TYPE: PRT
<213> ORGANISM: Artificial sequence
<220> FEATURE:
<223> OTHER INFORMATION: Derived from Homo Sapiens

<400> SEQUENCE: 65

Ser Glu Pro Ile Ser Pro Pro Arg Asp Arg
1               5                   10

<210> SEQ ID NO 66
<211> LENGTH: 11
<212> TYPE: PRT
<213> ORGANISM: Artificial
<220> FEATURE:
<223> OTHER INFORMATION: Derived from Homo Sapiens

<400> SEQUENCE: 66

Lys Asn Phe Ile Ala Val Ser Ala Ala Asn Arg
1               5                   10

<210> SEQ ID NO 67
<211> LENGTH: 11
<212> TYPE: PRT
<213> ORGANISM: Artificial
<220> FEATURE:
<223> OTHER INFORMATION: Derived from Homo Sapiens

<400> SEQUENCE: 67

Thr Asn Ser Asp Ile Val Glu Ala Leu Asn Lys
1               5                   10

<210> SEQ ID NO 68
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 68

Ile Ser Ser Ser Gly Ala Leu Asp Asp Asp Asp Lys
1               5                   10

<210> SEQ ID NO 69
<211> LENGTH: 10
<212> TYPE: PRT
<213> ORGANISM: Artificial
<220> FEATURE:
<223> OTHER INFORMATION: Derived from Homo Sapiens

<400> SEQUENCE: 69

Ile Gln Ile Thr Arg Ile Met Asp Glu Arg
1               5                   10

<210> SEQ ID NO 70
<211> LENGTH: 11
<212> TYPE: PRT
```

```
<213> ORGANISM: Artificial
<220> FEATURE:
<223> OTHER INFORMATION: Derived from Homo Sapiens

<400> SEQUENCE: 70

Leu Phe Gln Tyr Ala Ser Thr Asp Met Asp Lys
1               5                   10

<210> SEQ ID NO 71
<211> LENGTH: 12
<212> TYPE: PRT
<213> ORGANISM: Artificial
<220> FEATURE:
<223> OTHER INFORMATION: Derived from Homo Sapiens

<400> SEQUENCE: 71

Thr Asn Ser Asp Ile Val Glu Ala Leu Asn Lys Lys
1               5                   10

<210> SEQ ID NO 72
<211> LENGTH: 12
<212> TYPE: PRT
<213> ORGANISM: Artificial sequence
<220> FEATURE:
<223> OTHER INFORMATION: Derived from Homo Sapiens

<400> SEQUENCE: 72

Asn Phe Ile Ala Val Ser Ala Ala Asn Arg Phe Lys
1               5                   10
```

MASS SPECTROMETRIC BASED ASSAY FOR PRESENCE OF A PROTEIN WITHOUT THE USE OF A STANDARD

RELATED APPLICATIONS

This application is a continuation and the claims the right of priority under 35 U.S.C. §120 to U.S. application Ser. No. 11/580,221, filed Oct. 12, 2006, now abandoned, which claims priority to Provisional Patent Application No. 60/727,187, filed Oct. 13, 2005, the contents of both of which are hereby expressly incorporated by reference in their entirety as though fully set forth herein.

INTRODUCTION

In many applications of the analysis of a biological sample there is a desire to obtain absolute or relative quantitative information for a set of proteins present at low concentrations in the sample. This can be especially true in biomarker discovery and validation, and is non-trivial for several reasons, for example, extremely high sensitivity may be required to achieve appropriate detection limits and the complexity of the sample (e.g., large numbers of proteins present at concentrations spanning several orders of magnitude) may cause interferences that compromise the detection limit. In addition, although the protein of interest or its corresponding DNA sequence may be known, standard samples of the protein of interest may not be available; hence, the development of an assay or method that can quantitate the amount of protein in the sample can be extremely difficult.

Traditionally, most clinically relevant markers are detected by immunoassays that provide precise measures of serum protein levels in relation to disease progression or therapy. However, a growing number of candidate protein markers are being discovered through proteomic and transcriptional profiling methods and often there are no antibody reagents available for their precise quantification in human clinical samples. In addition, most clinically relevant biomarkers are present at low concentrations in biological samples. The development of practical approaches for the quantitative analysis of biomarkers across multiple samples derived from body fluids, tissues, or other biological matrices is necessary in order to confirm that these proteins are reliable predictors of disease and may eventually be used as a clinical diagnostic.

SUMMARY

The present teachings provide methods for the development of a mass spectrometric based assay for a protein in a sample using parent-daughter ion transition monitoring (PDITM). In various aspects, the present teachings provide methods for developing a mass spectrometric based assay for a protein in a sample without the use of a standard for the protein. In various embodiments, the sample comprises proteolytic fragments of a protein which is present in low abundance in the physiological fluid from which it is derived.

The methods of the present teachings can be applied to develop a mass spectrometric based assay for a protein present in any of a number of biological samples, including, but not limited to, physiological fluids, and cell or tissue lysates. The biological samples can be from different sources, conditions, or both; for example, control vs. experimental, samples from different points in time (e.g. to form a sequence), disease vs. normal, experimental vs. disease, contaminated vs. non-contaminated, etc. Examples of physiological fluids, include, but are not limited to, blood, serum, plasma, sweat, tears, urine, cerebrospinal fluid, peritoneal fluid, lymph, vaginal secretion, semen, spinal fluid, ascetic fluid, saliva, sputum, breast exudates, and combinations thereof.

In various embodiments, methods of the present teachings can be applied to develop a mass spectrometric based assay for a protein in blood at a concentration of less than about 100,000 attomoles/microliter, less than about 10,000 attomoles/microliter, less than about 1,000 attomoles/microliter, less than about 100 attomoles/microliter, less than about 10 attomoles/microliter, and/or less than about 1 attomoles/microliter. Such methods, for example, can be used in various embodiments to develop a protein biomarker assay.

To develop a mass spectrometric based protein assay, the present teachings use a mass spectrometric technique of parent-daughter transition monitoring. The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry) is selected to transmit a molecular ion (often referred to as "the parent ion" or "the precursor ion") to an ion fragmentor (e.g., a collision cell, photodissociation region, etc.) to produce fragment ions (often referred to as "daughter ions") and the transmitted m/z range of a second mass separator (often referred to as the second dimension of mass spectrometry) is selected to transmit one or more daughter ions to a detector which measures the daughter ion signal. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal". In the present teachings, where the parent ion is generated for a proteolytic fragment of a protein and the ion signal of a daughter ion is measured, the daughter ion signal at the detector for a given proteolytic fragment ion-daughter ion combination monitored can be referred to as the "parent-daughter ion signal".

The parent-daughter ion signal, and other ion signals described herein, can be based, for example, on the intensity (average, mean, maximum, etc.) of the daughter ion peak, the area of the daughter ion peak, or a combination thereof.

In various embodiments, parent-daughter ion transition monitoring comprises multiple reaction monitoring (MRM) (also referred to as selective reaction monitoring). In various embodiments of MRM, the monitoring of a given parent-daughter ion transition comprises using as the first mass separator a first quadrupole parked on the parent ion m/z of interest to transmit the parent ion of interest and using as a second mass separator a second quadrupole parked on the daughter ion m/z of interest to transmit daughter ions of interest. In various embodiments, a PDITM can be performed, for example, by parking the first mass separator on parent ion m/z of interest to transmit parent ions and scanning the second mass separator over a m/z range including the m/z value of the daughter ion of interest and, e.g., extracting an ion intensity profile from the spectra. A tandem mass spectrometer (MS/MS) instrument or, more generally, a multidimensional mass spectrometer (MS$^n$) instrument, can be used to perform PDITM, e.g., MRM. In various embodiments, the mass spectrometer is a triple quadrupole linear ion trap mass spectrometer.

In various aspects, the present teachings provide methods for developing a mass spectrometric based assay for a protein in a sample without the use of a standard for the protein, comprising the steps of: (a) predicting one or more of the proteolytic fragments of a protein based on one or more of an amino acid sequence for the protein and a translation of a gene sequence for the protein; (b) predicting one or more of the fragments produced from one or more of the proteolytic fragments of the protein when the proteolytic fragment is subjected to collision induced dissociation; (c) providing a sample containing proteolytic fragments of a protein; (d) loading at least a portion of the sample on a chromatographic column; (e) subjecting at least a portion of the eluent from the chromatographic column to multiple reaction monitoring, where the transmitted parent ion m/z range of each multiple reaction monitoring scan includes a m/z value of one or more of the predicted proteolytic fragments of the protein and the transmitted daughter ion m/z range of each multiple reaction monitoring scan includes a m/z value one or more of the predicted collision induced dissociation fragments of the of the predicted proteolytic fragments; (f) measuring the ion signal of the m/z value range encompassing one or more of the predicted collision induced dissociation fragments m/z value using said multiple reaction monitoring; (g) performing a substantially full product ion scan on a m/z value range encompassing a predicted proteolytic fragment m/z value when the measured ion signal corresponding to one or more collision induced dissociation fragments of the predicted proteolytic fragment is above a specified signal threshold; (h) measuring the ion signals associated with the parent-daughter ion transitions of said substantially full product ion scan; and (i) selecting as the parent-daughter ion transition for an assay of the presence of the protein in a biological sample a parent-daughter ion transition of said substantially full product ion scan, wherein the selected parent-daughter ion transition for the assay corresponds to a transition where the transmitted parent ion is a proteolytic fragment of said protein, and wherein the selected parent-daughter ion transition has, relative to the measured ion signals associated with the other parent-daughter ion transitions for said protein, one or more of the approximately highest parent-daughter ion signal and the approximately highest signal-to-noise ratio. In various embodiments, the step of measuring the ion signal of the m/z value range encompassing one or more of the predicted collision induced dissociation fragments m/z value comprises: (1) sequencing the transmitted parent ion when the measured ion signal corresponding to one or more collision induced dissociation fragments of the predicted proteolytic fragment is above the specified signal threshold; and (2) performing said substantially full product ion scan on a m/z value range encompassing said sequenced transmitted parent ion when the sequence of the sequenced transmitted parent ion corresponds to a proteolytic fragment of the protein. In various embodiments, this step of measuring the ion signal further comprises a step of measuring the charge state of the transmitted parent ion when the measured ion signal corresponding to one or more collision induced dissociation fragments of the predicted proteolytic fragment is above a specified signal threshold.

In various aspects, the present teachings provide methods for developing a mass spectrometric based assay for detecting a low abundance protein in a blood sample without the use of a standard for the protein comprising the steps of: (a) predicting one or more of the proteolytic fragments of a protein based on one or more of an amino acid sequence for the protein and a translation of a gene sequence for the protein; (b) predicting one or more of the fragments produced from one or more of the proteolytic fragments of the protein when the proteolytic fragment is subjected to collision induced dissociation; (c) providing a sample containing proteolytic fragments of a protein, wherein said sample is derived from a blood sample containing the protein in a concentration of less than about 100,000 attomoles/microliter; (d) loading at least a portion of the sample on a chromatographic column; (e) subjecting at least a portion of the eluent from the chromatographic column to multiple reaction monitoring, the transmitted parent ion m/z range of each multiple reaction monitoring scan including a m/z value of one or more of the predicted proteolytic fragments of the protein and the transmitted daughter ion m/z range of each multiple reaction monitoring scan including a m/z value one or more of the predicted collision induced dissociation fragments of the of the predicted proteolytic fragments; (f) measuring the ion signal of the m/z value range encompassing one or more of the predicted collision induced dissociation fragments m/z value using said multiple reaction monitoring; (g) performing a substantially full product ion scan on a m/z value range encompassing a predicted proteolytic fragment m/z value when the measured ion signal corresponding to one or more collision induced dissociation fragments of the predicted proteolytic fragment is above a specified signal threshold; (h) measuring the ion signals associated with the parent-daughter ion transitions of said substantially full product ion scan; and (i) selecting as the parent-daughter ion transition for an assay of the presence of the protein in a biological sample a parent-daughter ion transition of said substantially full product ion scan, wherein the selected parent-daughter ion transition for the assay corresponds to a transition where the transmitted parent ion is a proteolytic fragment of said protein, and wherein the selected parent-daughter ion transition has, relative to the measured ion signals associated with the other parent-daughter ion transitions for said protein, one or more of the approximately highest parent-daughter ion signal and the approximately highest signal-to-noise ratio. In various embodiments, the step of measuring the ion signal of the m/z value range encompassing one or more of the predicted collision induced dissociation fragments m/z value comprises: (1) sequencing the transmitted parent ion when the measured ion signal corresponding to one or more collision induced dissociation fragments of the predicted proteolytic fragment is above the specified intensity threshold; and (2) performing said substantially full product ion scan on a m/z value range encompassing said sequenced transmitted parent ion when the sequence of the sequenced transmitted parent ion corresponds to a proteolytic fragment of the protein. In various embodiments, this step of measuring the ion signal further comprises a step of measuring the charge state of the transmitted parent ion when the measured ion signal corresponding to one or more collision induced dissociation fragments of the predicted proteolytic fragment is above a specified signal threshold.

In various aspects, the present teachings provide methods for developing a mass spectrometric assay for a protein in a sample without the use of a standard for the protein comprising the steps of: (a) predicting one or more of the proteolytic fragments of a protein based on one or more of an amino acid sequence for the protein and a translation of a gene sequence for the protein; (b) predicting one or more of the fragments produced from one or more of the proteolytic fragments of the protein when the proteolytic fragment is subjected to collision induced dissociation; (c) providing a sample containing proteolytic fragments of a protein; (d) loading at least a portion of the sample on a chromatographic column; (e) subjecting at least a portion of the eluent from the chromatographic column to multiple reaction monitoring, the transmitted parent ion m/z range of each multiple reaction monitoring scan including a m/z value of one or more of the predicted proteolytic fragments of the protein and the transmitted daughter ion m/z range of each multiple reaction monitoring scan including a m/z value one or more of the predicted collision induced dissociation fragments of the of the predicted proteolytic fragments; (f) measuring the ion signal of the m/z value range encompassing one or more of the predicted collision induced dissociation fragments m/z value using said multiple reaction monitoring; (g) measuring the charge state of the transmitted parent ion when the measured ion signal corresponding to one or more collision induced dissociation fragments of the predicted proteolytic fragment is above a specified signal threshold; (h) sequencing the transmitted parent ion when the measured ion signal corresponding to one or more collision induced dissociation fragments of the predicted proteolytic fragment is above the specified signal threshold; (i) performing a substantially full product ion scan on a m/z value range encompassing said sequenced transmitted parent ion when the sequence of the sequenced transmitted parent ion corresponds to a proteolytic fragment of the protein; (j) measuring the ion signals associated with the parent-daughter ion transitions of said substantially full product ion scan; and (k) selecting as the parent-daughter ion transition for an assay of the presence of the protein in a biological sample the parent-daughter ion transition which has, relative to the measured ion signals associated with the other parent-daughter ion transitions for said protein, one or more of the approximately highest parent-daughter ion signal and the approximately highest signal-to-noise ratio.

As understood by one of ordinary skill in the art, the term "full product ion scan" refers to a mass spectrometric scan over m/z values corresponding to product ions of a parent ion that has been subjected to fragmentation. As used herein, the term "full to product ion scan" does not require that scans encompass all m/z values from zero up to the highest m/z value possible for a product ion. As understood by those of ordinary skill in the art, mass spectrometers can be limited in the lower m/z value limit they can effectively reach and product ions below a certain mass may not be of interest, e.g., free hydrogen ion fragments ($H^+$). For example, a mass spectrometric scan for product ions from about 30 amu to a m/z value corresponding to the highest possible product ion mass can be considered a "full product ion scan" even though ions with a mass of less than about 30 amu will not be scanned or detected.

In various embodiments of the various aspects of the present teachings, an assay for the presence of one or more specific proteins (e.g., biomarker proteins) in a biological sample is developed where the protein is present in low abundance in the sample such as, for example, a blood sample. In various embodiments, the sample contains the protein in a concentration of less than about 100,000 attomoles/microliter, less than about 10,000 attomoles/microliter, less than about 1,000 attomoles/microliter, less than about 100 attomoles/microliter, less than about 10 attomoles/microliter, and/or less than about 1 attomoles/microliter. In various embodiments, mass spectrometric based assay for a protein in a sample of the present teachings can be extended to lower protein concentrations, e.g., by reducing the dynamic range of the protein concentration in the sample. For example, detection of lower concentrations of a protein of interest in a complex mixture can be achieved by removal of more abundant proteins, enrichment of the protein of interest in the sample, or combinations thereof, to increase, for example, the relative amount of the protein of interest in the sample loaded on the chromatographic column.

In various embodiments, the sample is prepared from extracts of cells, tissues and physiological fluids. Examples of physiological fluids, include, but are not limited to, blood, serum, plasma, sweat, tears, cerebrospinal fluid, urine, peritoneal fluid, lymph, vaginal secretion, semen, spinal fluid, ascetic fluid, saliva, sputum, breast exudates, and combinations thereof. The samples can be derived from different sources, conditions, or both; for example, control vs. experimental, samples from different points in time (e.g. to form a sequence), disease vs. normal, experimental vs. disease, contaminated vs. non-contaminated, etc.

A wide variety of approaches can be used to generate proteolytic fragments of the protein of interest. Suitable techniques for generating proteolytic fragments from proteins include any sequence specific cleavage process. Examples of suitable enzymatic sequence specific cleavage techniques include cleavage with proteases, such as, for example, serine proteases, and thiol proteases. For example, proteolytic fragments (e.g., peptides) can be generated from a protein by the enzymatic hydrolysis of peptide bonds with trypsin to produce a plurality of peptide proteolytic fragments.

In various embodiments, the sample containing proteolytic fragments of a protein further comprises a concentration standard for one or more of the predicted proteolytic fragments of the protein that is created after, and based on, the present teachings select the proteolytic fragment for use as an assay for said protein. The concentration standard can be, for example, a stable isotope labeled peptide corresponding to one of the proteolytic peptides generated from the protein of interest.

In various aspects, provided are assays designed to determine the presence of a protein of interest in one or more samples. The assay can be, for example, a biomarker validation assay, used to aid in the discovery of various biochemical pathways, for drug discovery or a diagnostic assay. The assay can, for example, be diagnostic of a disease or condition, prognostic of a disease or condition, or both.

In various aspects, the present teachings provide articles of manufacture where the functionality of a method of the present invention is embedded as computer-readable instructions on a computer-readable medium, such as, but not limited to, a floppy disk, a hard disk, an optical disk, a magnetic tape, a PROM, an EPROM, CD-ROM, or DVD-ROM.

BRIEF DESCRIPTION OF THE DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings.

DETAILED DESCRIPTION OF VARIOUS EMBODIMENTS

Figure 1:
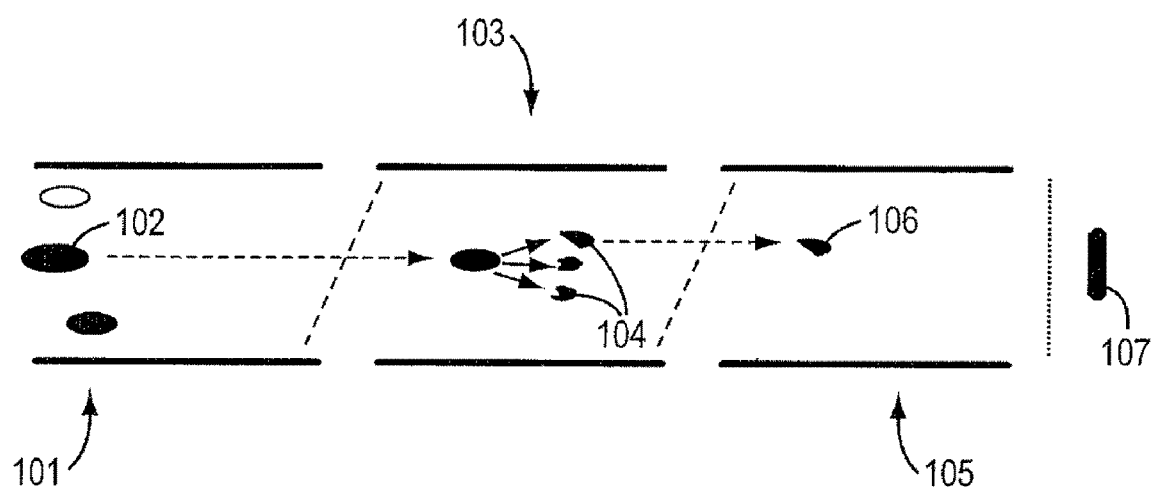
FIG. 1 is a simplified schematic diagram of the mass spectrometer system used in the Examples.

To develop a mass spectrometric based protein assay, the present teachings use a mass spectrometric technique of parent-daughter ion transition monitoring. In various embodiments, parent-daughter ion transition monitoring comprises multiple reaction monitoring (MRM). Referring to FIG. 1, a MRM scan can be conducted, for example, by setting a first mass separator 101 to transmit the mass of a proteolytic fragment of interest (i.e., the parent ion 102) to the ion fragmentor 103. The first mass separator 101 can be set, e.g., by setting the first mass separator to transmit ions in a mass window about 3 mass units wide substantially centered on the mass of a proteolytic fragment. In various embodiments, the collision energy of the ion fragmentor 103 can be selected to facilitate producing the selected charged fragment of this peptide (the daughter ion) in the ion fragmentor (here, the ion fragmentor comprises a collision gas for conducting CID and a quadrupole, to facilitate, e.g., collecting ion fragments 104 and fragment ion transmittal). The second mass separator 105 is set to transmit the daughter ion (or ions) 106 of interest (e.g., by setting the second mass separator to transmit ions in a mass window about 1 mass unit wide substantially centered on the mass of a daughter ion) to a detector 107 to generate an ion signal for the daughter ion (or ions) transmitted.

In various embodiments, MRM parameters, for each parent ion-daughter ion combination, can be chosen to facilitate optimizing the signal for the selected daughter ion (or ions) associated with that parent ion (proteolytic fragment of the protein of interest). In various embodiments, dwell times typically between, but not limited to, about 10 ms to about 200 ms can be used on the mass separators in this experiment and the ability to rapidly change between MRM transitions can allow multiple components in a mixture to be monitored in a single LC-MS run. For example, 50-100 different components can be monitored in a single time period in a single LC-MS run. The use of specific time periods can allow more MRM transitions to be monitored in a single LC-MS run.

A wide variety of mass analyzer systems can be used in the present teachings to perform PDITM. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, or combinations thereof.

Examples of suitable mass spectrometry systems for the mass analyzer include, but are not limited to, those which comprise a triple quadrupole, a quadrupole-linear ion trap, a quadrupole TOF systems, and TOF-TOF systems.

Suitable ion sources for the mass spectrometry systems include, but are not limited to, electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

In various embodiments, the mass spectrometer system comprises a triple quadrupole mass spectrometer for selecting a parent ion and detecting fragment daughter ions thereof. In various embodiments, the first quadrupole selects the parent ion, herein referred to as Q1. The second quadrupole, herein referred to as Q2, is maintained at a sufficiently high pressure and voltage so that multiple low energy collisions occur causing some of the parent ions to fragment. The third quadrupole, Q3, is selected to transmit the selected daughter ion to a detector.

In various embodiments, one or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole Q1 selects the parent ion. The second quadrupole Q2 is maintained at a sufficiently high collision gas pressure and voltage so that multiple low energy collisions occur causing some of the parent ions to fragment. The third quadrupole Q3 is selected to trap fragment ions and, after a fill time, transmit the selected daughter ion to a detector by, e.g., pulsing an end electrode to permit the selected daughter ion to exit the ion trap. Desired fill times can be determined, e.g., based on the number of fragment ions, charge density within the ion trap, the time between elution of different peptides, duty cycle, decay rates of excited state species or multiply charged ions, or combinations thereof.

Figure 2B:
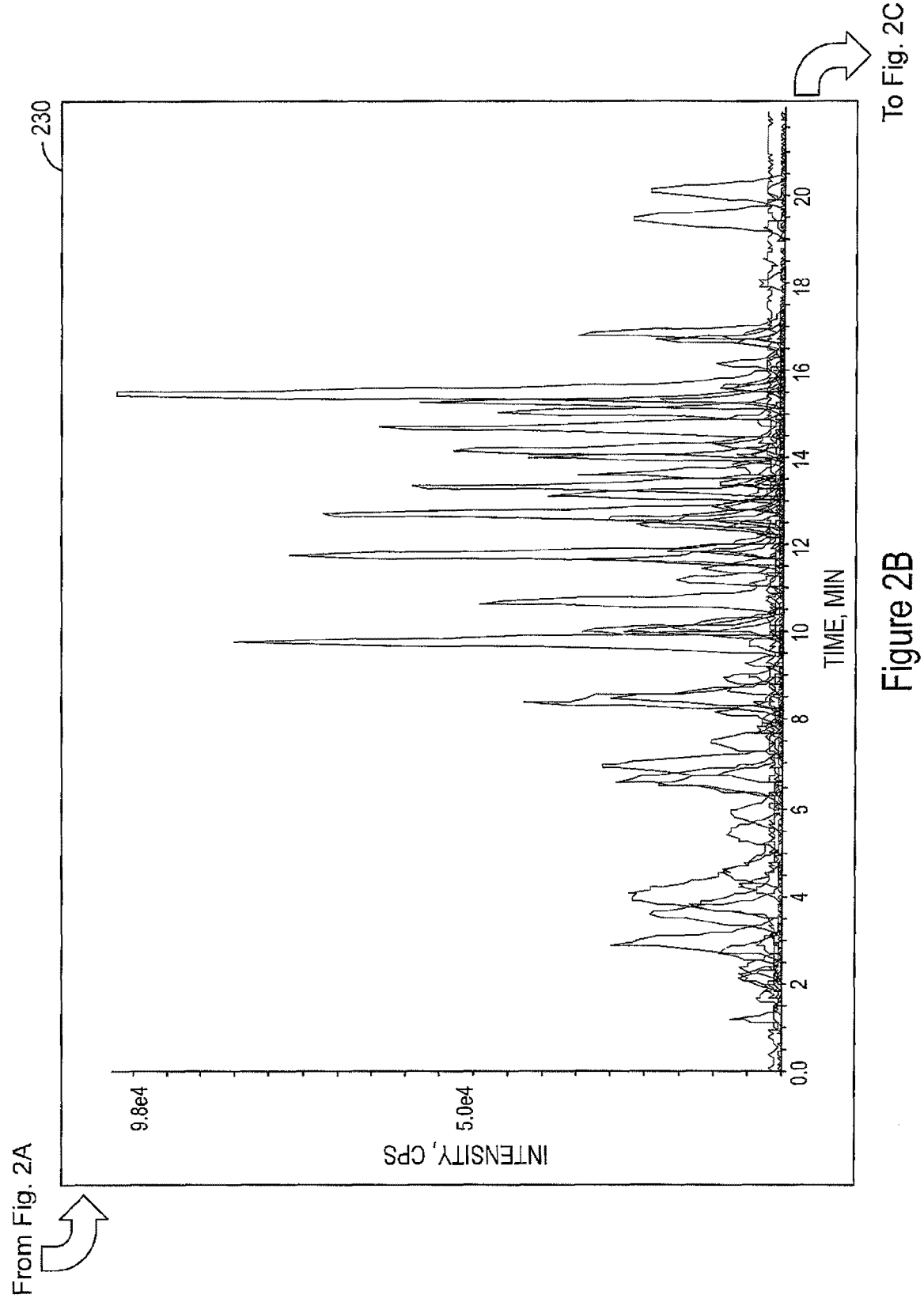
FIG. 2 schematically depicts various embodiments of a method for the development of an MRM-based assay for the validation of biomarkers.
Figure 2C:
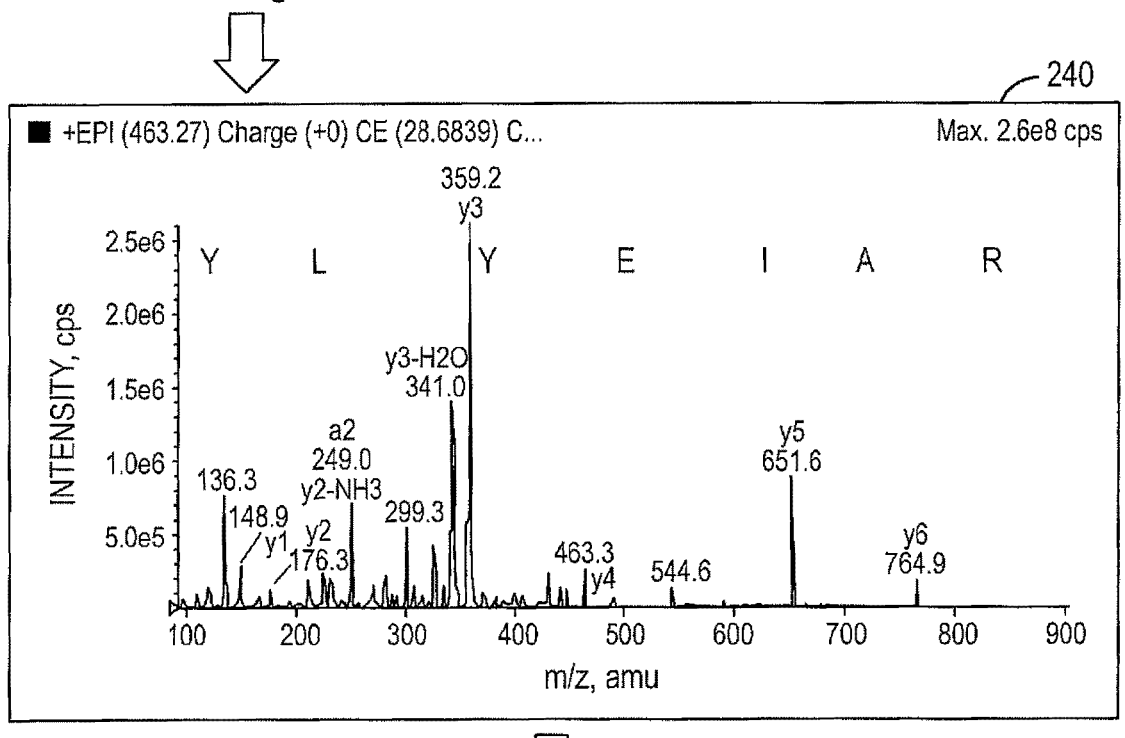
Figure 2C:
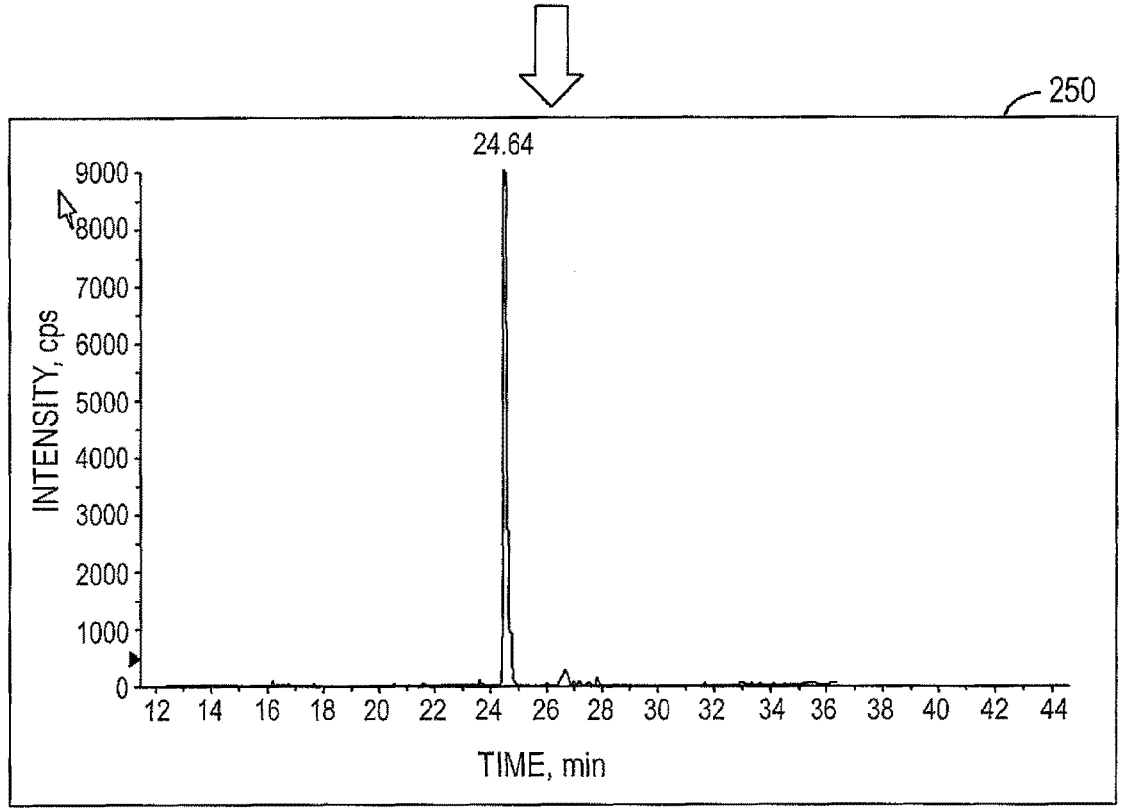

Referring to FIG. 2, depicted is a schematic diagram illustrating various embodiments of the present teachings for developing a mass spectrometric based assay for the detection of the presence of a protein in a sample. In various embodiments, the present teachings determine initial putative MRM transitions for the protein of interest based on a known or predicted sequence of the protein of interest. Protein sequence information can obtained from a number of sources, including, but not limited to, amino acid sequence databases (e.g., Celera, SwissProt, etc.), DNA databases, translations of a gene sequence, direct experimental determination, and combinations thereof. The methods of the present invention predict from the protein sequence 210 the proteolytic to fragments of the protein (e.g., peptide fragments) and predict the fragments (daughter ions) of these proteolytic fragments that result from fragmentation of the proteolytic fragment by the fragmentation method of the ion fragmentor. In various embodiments, the ion fragmentation method comprises collision-induced-dissociation (CID), and the predicted daughter ions are those that result from CID of the corresponding proteolytic fragment. Accordingly, the proteolytic fragments (e.g., peptides) generated from a theoretical proteolysis of the protein can be used to determine one or more daughter ions for the corresponding proteolytic fragment and thereby determine initial parent-daughter ion transitions 220 for monitoring by MRM. These transitions are often listed using the notation MS1/MS2, where MS1 refers to the nominal mass-to-charge ratio transmitted by the first mass separator (and hence the nominal proteolytic fragment m/z) and MS2 refers to the nominal m/z transmitted by the second mass separator (and hence the nominal proteolytic fragment daughter ion m/z).

A sample, which contains proteolytic fragments of the protein of interest, is then subjected to an MRM experiment. Prior to the MRM experiment, the sample can be subjected to processing steps to, for example, concentrate the sample, fractionate out interfering sample, remove at least a portion of the more abundant proteins, etc. At least a portion of the sample is loaded onto a chromatographic column and at least a portion of the eluent is directed to a mass spectrometry system. The mass spectrometry system is used to perform MRM using one or more of the initial parent-daughter ion transitions, and the parent-daughter ion transition signals are measured 230. To confirm the identity of the peptides being detected by MRM, an information-dependent acquisition experiment can be used to obtain dependent MS and MS/MS spectra of the peptides 240. In various embodiments, for example, when the ion signal is above a specified signal threshold, a substantially full product ion scan is performed on the corresponding proteolytic fragment. In various embodiments, when the ion signal is above a specified signal threshold, several linear ion trap scans are triggered, to provide, e.g., an enhanced resolution scan (a high-resolution scan using the linear ion trap) to confirm the charge state and monoisotopic mass of the peptide, and/or an enhanced product ion scan (an MS/MS scan using the linear ion trap) to confirm the sequence of the peptide.

For example, a full product ion scan can be performed on the transmitted parent ion and the parent ion sequenced in order to confirm the identity of the detected parent ion as a predicted proteolytic fragment from the desired protein. Preferably, the parent ions are fragmented in a collision cell to a series of fragment ions, among which are a ladder of ions with sequentially decreasing numbers of amino acids. Since the fragmentation can occur anywhere along the peptide, a spectrum of the observed mass to charge ratios is generated. Typically, two prominent sets of ions are observed in the fragmentation spectrum. One set is a sequence ladder with amino acid deletions from the C-terminal end of the peptide (often referred to as the y series), while the other set is a sequence ladder with amino acid deletions from the N-terminal end (often referred to as the b series). Complete or partial amino acid sequence information for the parent ions is then obtained by interpretation of the fragmentation spectra. As the different amino acids within a peptide each have different masses, the fragmentation spectrum of a peptide is usually characteristic of the peptide sequence.

In various embodiments, the experimentally measured full scan MS/MS spectra are used to refine the initial predicted parent-daughter ion transitions to generate a refined set of PDITs and the step of performing MRM and measuring the resultant parent-daughter ion transition signals are measured 230 is repeated using one or more of the refined parent-daughter ion transitions. This process of refining and measuring can be repeated.

The methods of the present teachings then select a parent-daughter ion transition as an assay of the presence of the protein in the biological sample 250. The parent-daughter ion transition is selected based on (i) the parent ion of the parent-daughter ion transition is a proteolytic fragment of said protein; and at least one of the following, (ii) the selected parent-daughter ion transition has, relative to the measured ion signals associated with the other parent-daughter ion transitions for the protein, the approximately highest ion signal (as determined by peak area in this Example); (iii) the selected parent-daughter ion transition has, relative to the measured ion signals associated with the other parent-daughter ion transitions for the protein, the approximately highest signal-to-noise ratio; (iv) the selected parent-daughter ion transition has, relative to the measured ion signals associated with the other parent-daughter ion transitions for the protein, the ion signal with the approximately smallest amount of error in the ion signal; and/or (v) the selected parent-daughter ion transition has one or more of a lower limit of quantitation (LOQ), signal-to-noise ratio, and/or parent-daughter ion signal, greater than a specified threshold value.

In various embodiments, the daughter ions for the selected parent-daughter ion transition can be selected based on one or more of their: level of detection (LOD), limit of quantitation (LOQ), signal-to-noise (S/N) ratio, mass similarity with other daughter ions of other peptides, etc. In various embodiments, the LOQ ranges from about attomole levels ($10^{-18}$ moles) to about femtomole levels ($10^{-15}$ moles) of sample on the LC column used, with a dynamic range of about three to about four orders of magnitude above the LOQ.

In various embodiments, the methods of the present teachings include a step of sample preparation to increase the sensitivity of the assay (e.g, to facilitate detecting lower protein concentrations). Several approaches can be used to increase the sensitivity of the assay, including, but not limited to, reducing the dynamic range of the protein concentration in the sample, increasing the relative concentration of the protein of interest in the sample, and combinations thereof. For example, lower concentrations of a protein of interest can be achieved by removal of more abundant proteins, enrichment of the protein of interest in the sample, or combinations thereof, to increase, for example, the relative amount of the protein of interest in the sample loaded on the chromatographic column. Although, mass spectrometers can theoretically detect a single molecule, typical chromatographic columns have practical limits to the amount of protein that can loaded on them.

In various embodiments, the sample containing proteolytic fragments of a protein further comprises a concentration standard for one or more of the predicted proteolytic fragments of the protein that is created after, and based on, the present teachings select the proteolytic fragment for use as an assay for said protein. The concentration standard can be, for example, a stable isotope labeled peptide corresponding to one of the proteolytic peptides generated from the protein of interest. It is to be understood that in various embodiments the present teachings provide methods for the development of a mass spectrometric based assay for a protein in a sample without the use of a standard for the protein. In various embodiments, the present teaching thus provide methods for determining the concentration standard, if any, to be used in a mass spectrometric assay for a protein in a sample.

In another aspect of the present teachings, the functionality of the methods described above may be implemented as computer-readable instructions on a general purpose computer. The computer may be separate from, detachable from, or integrated into a mass spectrometry system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer.

For example, the computer-readable instructions could be implemented in Intel 80×86 assembly language if it were configured to run on an IBM PC or PC clone. In one embodiment, the computer-readable instructions be embedded on an article of manufacture including, but not limited to, a computer-readable program medium such as, for example, a floppy disk, a hard disk, an optical disk, a magnetic tape, a PROM, an EPROM, CD-ROM, DVD-ROM.

The following examples illustrate experiments which use various principles of the present teachings. The teachings of these examples are not exhaustive and are not intended to limit the scope of the present teachings.

Example 1

Detection and Confirmation of Fibronectin in Depleted Human Plasma

In this example, the detection and confirmation of fibronectin in human plasma (which was depleted of the 6 typically highest abundance plasma proteins: albumin, IgG, IgA, transferrin, haptoglobin, and antitrypsin) is shown. This can be a valuable step in the confirmation of the assay; e.g., to have sequence confirmation information (full scan MS/MS) for every MRM transition at the specific retention time to be used for quantitation, for increased confidence in assay results. Fibronectin is typically present in human plasma at a concentration of about 5397 amol/μL.

Preparation of Sample

Figure 3A:
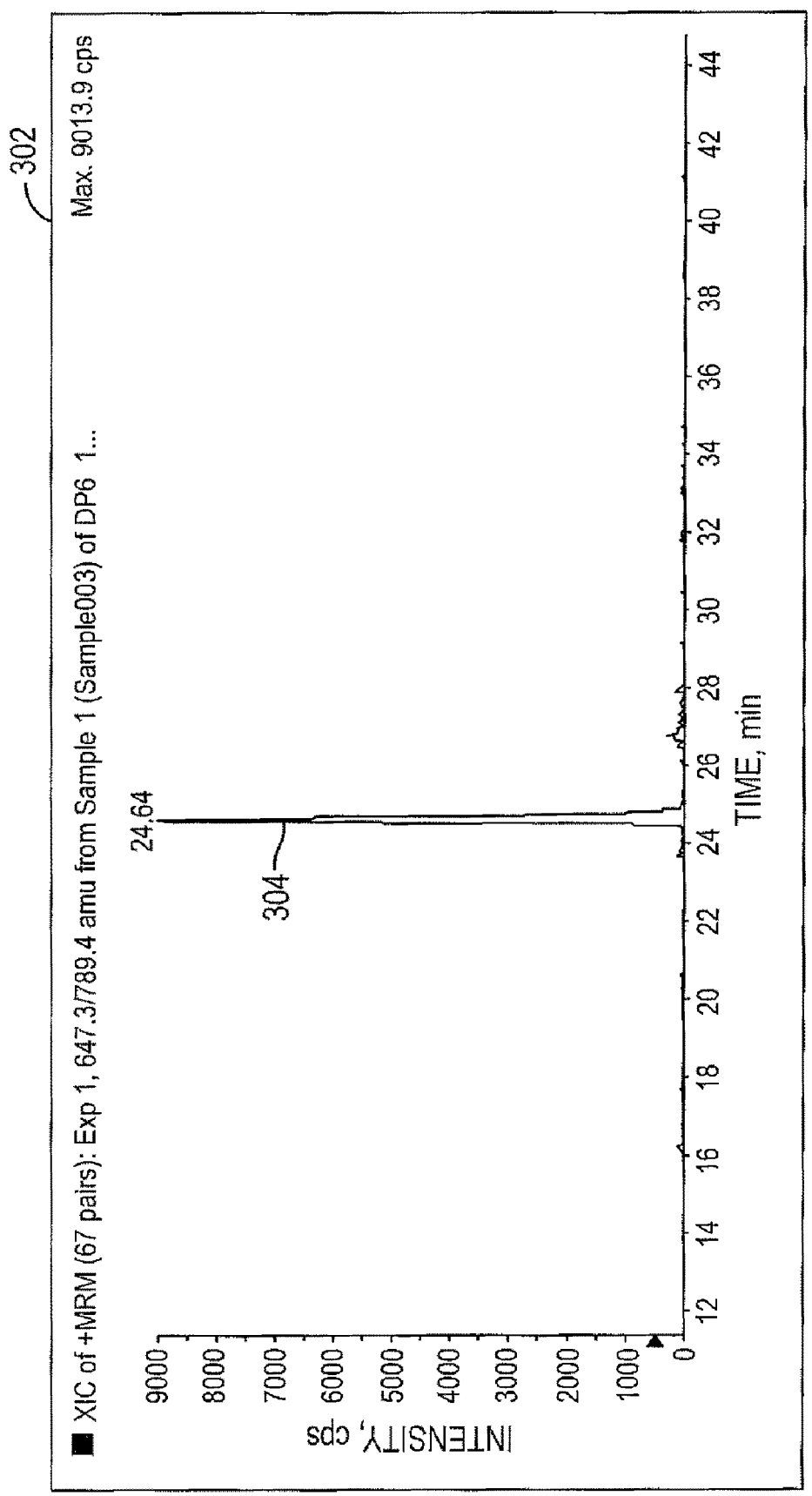
FIGS. 3A and 3B depict MRM and MS/MS experimental on a fibronectin peptide as discussed in Example 1.
Figure 3B:
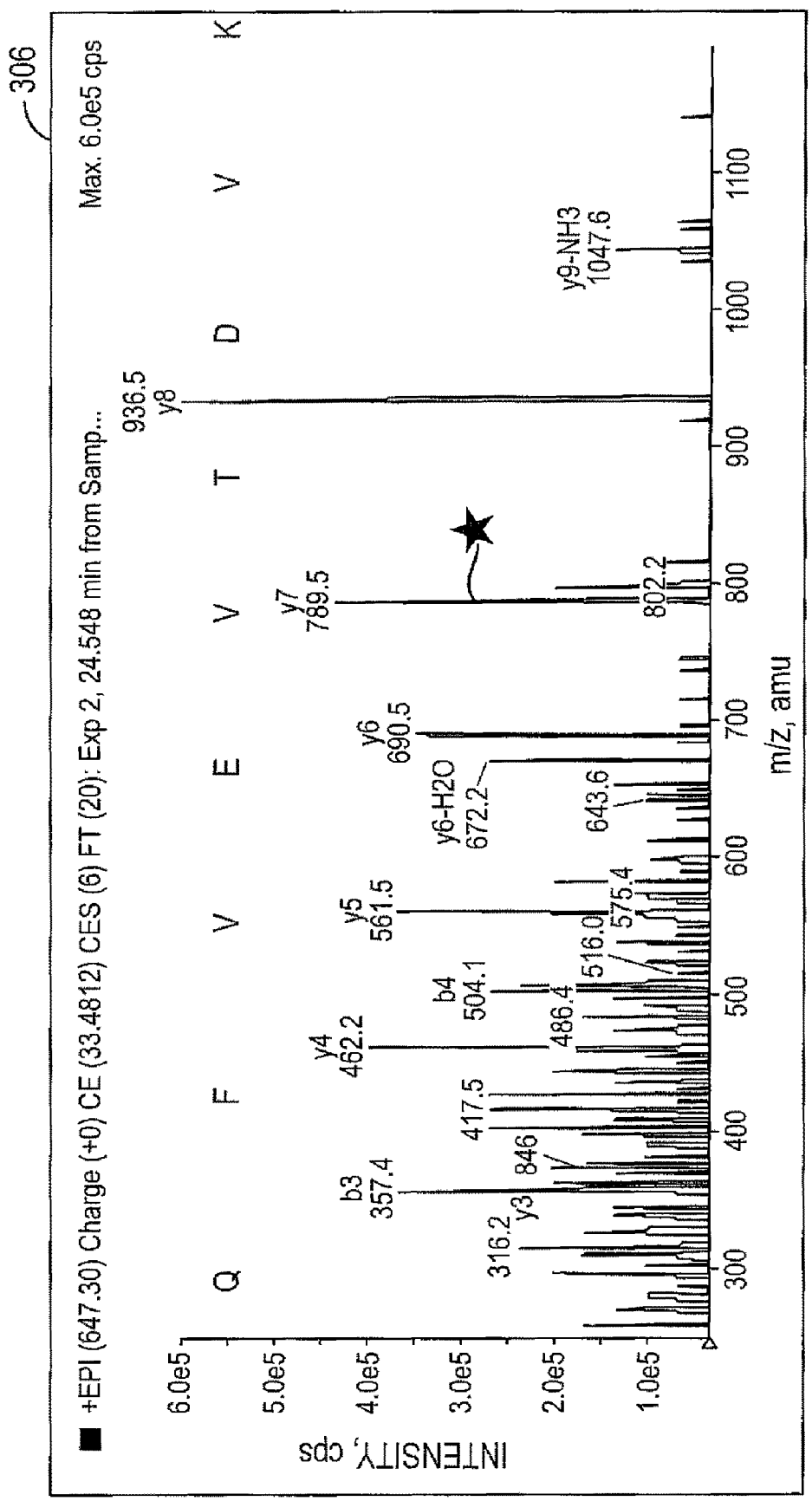

In this Example, the sample comprised human plasma. The plasma sample was depleted of the 6 typically highest abundant proteins (albumin, IgG, IgA, transferrin, haptoglobin, and antitrypsin) using the Multiple Affinity Removal System ("MARS" spincolumn: Agilent Technologies), and the samples desalted by filtration prior to loading on the chromatographic column. The plasma samples were also denatured, reduced, alkylated and then digested with trypsin prior to column loading.
Chromatography Human plasma (0.01 μL) was loaded on a C18 column (75 μm×15 cm, LC Packings) and components separated by reversed-phase HPLC using a 40 minute gradient (2-35% acetonitrile in 0.1% formic acid). In some cases, a precolumn desalting step was used (C18 trap, 300 μm×5 mm, LC Packings).
Mass Analyzer System MRM analysis was performed using the NanoSpray® source on an Applied Biosystems/MDS Sciex 4000 Q TRAP® system (Q1—unit resolution, Q3—unit resolution). MRM transitions for each peptide were either predicted based on MS/MS spectra or designed based on the peptide sequence. MRM-Initiated Detection and Sequencing using a MIDAS™ brand workflow as illustrated was used to confirm every MRM transition and retention time in the final assay.
Discussion FIG. 3A shows a MRM transition (647.3/789.4) for DLQFVEVTDVK peptide of fibronectin 302 for about 0.01 μL of plasma loaded onto a chromatography column (i.e., a loaded sample with about 54 amol of the protein). FIG. 3A also shows an MRM transition signal 304 for this Example. In this Example, the detection of the peptide by MRM drives the acquisition of MS/MS to confirm the peptide sequence and identify the detected peptide by a MS/MS experiment to provide sequence information on the daughter ion of the proteolytic fragment (peptide) of fibronectin. FIG. 3B provides an example of such MS/MS data 306. Although the digested sample is a highly complex mixture of peptides (proteolytic fragments), only a single peak is observed in the MRM survey scan data 304. The full product ion scan MS/MS data 306 shown in FIG. 3B (stars shows Q3 mass used in MRM of FIG. 3A) was used to confirm that the single peak observed in the MRM scan 304 is DLQFVEVTDVK, the targeted proteolytic fragment (peptide) from fibronectin. This example illustrates that peptides from the targeted protein of interest which, although present in low abundance, can be detected by MRM and confirmed by MS/MS in a complex biological mixture.

Example 2

Assessments on Whole and Depleted Human Plasma Samples

This Example provides data and assessment of various embodiments of the present teachings as applied to peptides (protein proteolytic fragments) representing 53 proteins in human plasma using a multiplexed approach. Of these, 47 produced quantitative data within-run coefficients of variation (CV) (n=10) of 2-22% (78% of assays had CV<10%). A number of peptides gave CV's in the range 2-7% in 5 experiments (10 replicate runs each) continuously measuring 137 MRM's, demonstrating the precision achievable in complex digests using the present teachings. Depletion of 6 the typically high abundant proteins by immunosubtraction (as described below) improved CV's compared to whole plasma, but analytes could be detected in both sample types (depleted and undepleted). Replicate digest and depletion/digest runs yielded correlation coefficients ($R^2$) of >99.5% and >98.9% respectively. Absolute analyte specificity for each peptide was demonstrated using MRM-triggered MS/MS scans. Reliable detection of L-selectin (measured at 0.67 μg/ml) and fibronectin indicate that proteins down to the υg/ml level can be quantitated in plasma with minimal sample preparation, yielding a dynamic range of about 4 to 5 orders of magnitude in a single experiment. In various embodiments, additional upfront sample preparation can be performed to facilitate detection of lower abundance proteins using the present teachings. Thus, in various embodiments, the present teachings can provide a robust platform for biomarker validation.

Figure 4A:
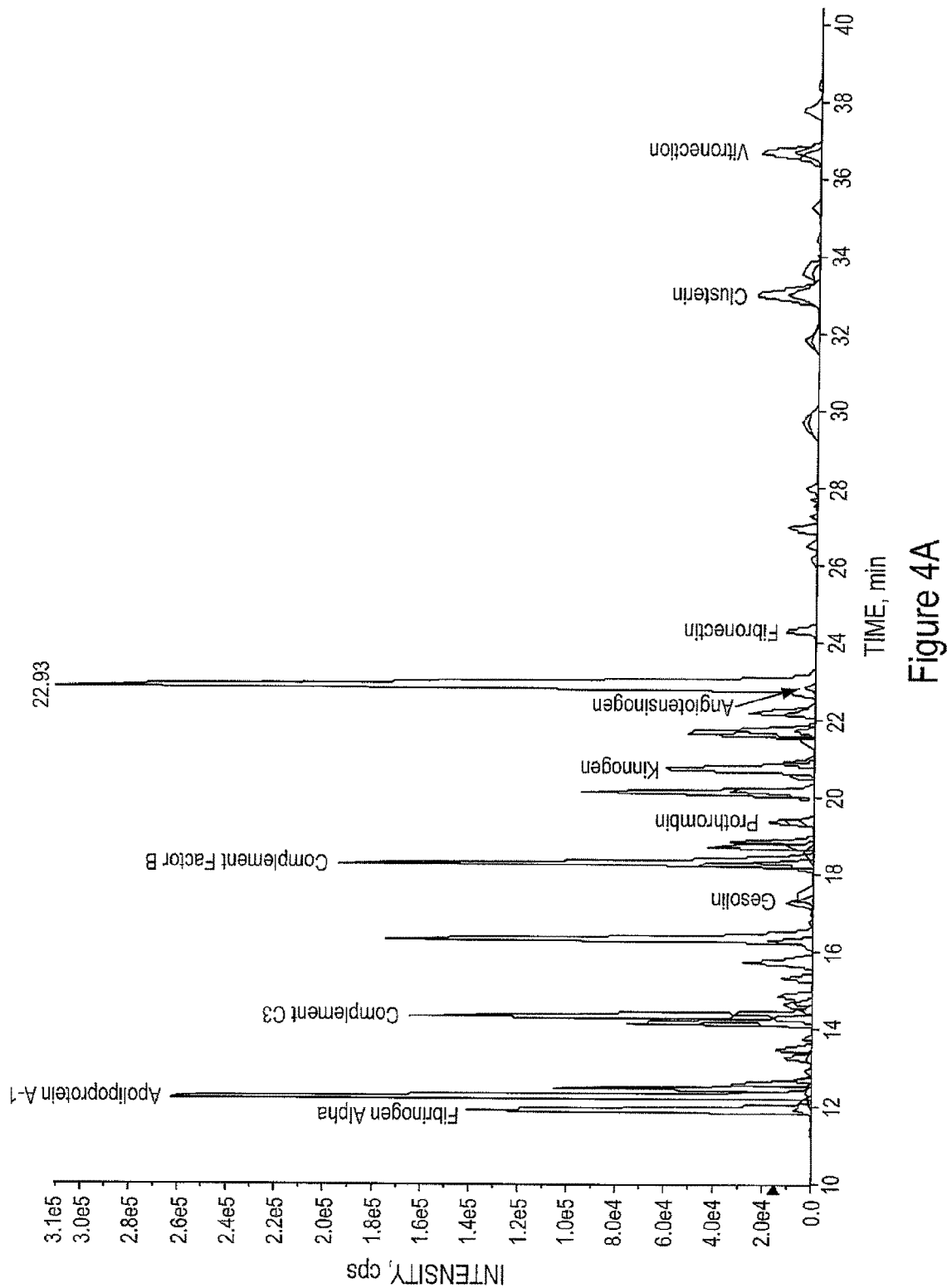
FIG. 4A depicts data for the peptides of the 53 proteins of Example 2 and FIG. 4B depicts the range of abundance of these proteins in the samples analyzed in Example 2.
Figure 4B:
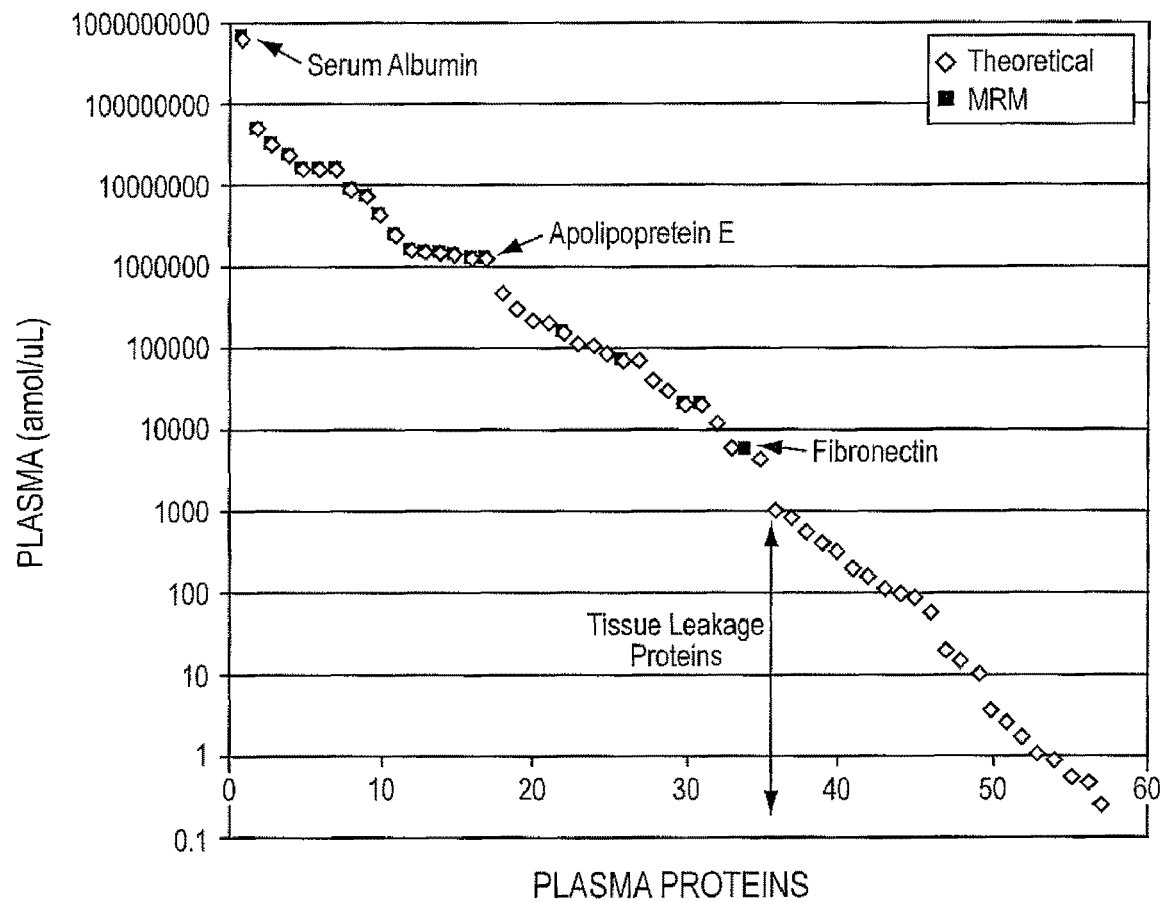

FIG. 4A depicts LC chromatogram data for the peptides of the 53 proteins (only 10 proteins are labeled due to space considerations in the figure) and FIG. 4B depicts the range of abundance of these proteins in the samples analyzed in this Example. The diamond-shaped symbols in FIG. 4B represent theoretically predicted values and the square-shaped symbols representing experimental results of this example.
Reagents Chemicals were obtained as follows: trypsin (Promega), sodium dodecyl sulfate (Bio-Rad Laboratories), iodoacetamide (Sigma), formic acid (Sigma), tris-(2-carboxyethyl) phosphine (Sigma) and acetonitrile (Burdick and Jackson).
Sample Protein Depletion and Digestion All experiments were performed on aliquots of a single human plasma sample from a normal volunteer. For the depleted sample preparation, the six typically highest abundant proteins were depleted from the plasma using the Multiple Affinity Removal System ("MARS" spincolumn: Agilent Technologies) substantially according to the manufacturer's recommended protocol. Depleted sample was then exchanged into 50 mM ammonium biocarbonate using a VivaSpin concentrator (5000 MWCO, VivaScience). Undepleted plasma was also desalted before digestion.

Both depleted or undepleted plasma samples were denatured and reduced by incubating proteins in 0.05% SDS and 5 mM tris-(2-carboxyethyl)phosphine at 60° C. for 15 minutes. The sample was then made 10 mM in iodoacetamide and incubated for 15 minutes at 25° C. in the dark. Trypsin was added in one aliquot (protease:protein ratio of 1:20) and incubated for 5 hours at 37° C.

Prediction of Proteolytic Fragments of the Proteins

In the present Example, three basic approaches were taken to prediction of the protein proteolytic fragments and MRM transitions: (1) in silico digestion from sequence databases and prediction of CID peptide fragment ions, (2) prediction from available LC-MS/MS proteomics survey data, and (3) the present teachings, a comprehensive MRM testing of all of a protein's candidate peptides using the MIDAS™ workflow. To further assess the methods of the present teachings, random MRM transitions were also generated.

In Silico

The in silico methods assembled a set of 177 proteins and protein forms that are demonstrated or potential plasma markers of some aspect of cardiovascular disease (see, e.g., Anderson, N. L. (2005) Candidate-based proteomics in the search for biomarkers of cardiovascular disease. *J Physiology* 563.1, 23-60, the entire contents of which is incorporated herein by reference) and a subset of 62 proteins selected for which an estimate of normal plasma abundance was available. Predicted tryptic peptides for each of these were generated, along with relevant Swissprot annotations and a series of computed physico-chemical parameters: e.g., amino acid composition, peptide mass, Hoop-Woods hydrophilicity (see, e.g., Hopp, T. P. and Woods, K. R. (1981) Prediction of protein antigenic determinants from amino acid sequences. *Proc Natl Acad Sci USA* 78, 3824-8, the entire contents of which is incorporated herein by reference) and predicted retention time in reversed-phase (C18) chromatography (see, e.g., Krokhin, O. V., Craig, R., Spicer, V., Ens, W., Standing, K. G., Beavis, R. C. and Wilkins, J. A. (2004) An improved model for prediction of retention times of tryptic peptides in ion pair reversed-phase hplc: Its application to protein peptide mapping by off-line hplc-maldi ms. *Mol Cell Proteomics* 3, 908-19, the entire contents of which is incorporated herein by reference). An index of the likelihood of experimental detection was derived from a data set reported by Adkins (Adkins, J. N., Varnum, S. M., Auberry, K. J., Moore, R. J., Angell, N. H., Smith, R. D., Springer, D. L. and Pounds, J. G. (2002) Toward a human blood serum proteome: Analysis by multi-dimensional separation coupled with mass spectrometry. *Mol Cell Proteomics* 1, 947-55.) the entire contents of which is incorporated herein by reference, by counting the number of separate "hits" for the peptide in the data set divided by the number of hits for the most frequently detected peptide from the same protein. An overall index of peptide quality was generated according to a formula that gave positive weights to P, KP, RP and DP content, and negative weights to C, W, M, chymotrypsin sites, certain SwissProt features (carbohydrate attachment, modified residues, sequence conflicts, or genetic variants), and mass less than 800 or greater than 2000. The 3619 tryptic peptides predicted for the 62 protein marker candidates (6 to 497 peptides per target) ranged in length from 1 to 285 amino acids. Within the range of 8-24 aminoacids, 721 peptides had a c-terminal Lys and 690 a c-terminal Arg. In this Example, peptides from 30 of these target proteins ending in C-terminal Lyswere selected for further study. Finally, based on simple CID fragmentation rules, the fragment ions were predicted and used to create the MRM transitions (e.g., the first and second y ion above the parent m/z value).

LC-MS/MS Proteomics Survey Data

Peptides were also selected based on a direct proteomics survey experiment. In this case a classical LC-MS/MS analysis of plasma digests in which the major ions observed by full scan MS were subjected to MS/MS using the ion trap capabilities of the 4000 Q TRAP instrument was carried out. The identified peptides showing the relatively best signal intensity and chromatographic peak shape for a given parent protein were selected. In addition, the GPM database of Beavis (see, e.g., Craig, R., Cortens, J. P. and Beavis, R. C. (2004) Open source system for analyzing, validating, and storing protein identification data. *J Proteome Res* 3, 1234-42, the entire contents of which is incorporated herein by reference) was used to select peptides from target proteins that were frequently detected (multiple experiments). From the full scan MS/MS data, the most intense y-ion observed was used as the fragment ion for the MRM transition.

MRM Testing

An adaptation of the MIDAS™ brand workflow was also used (see, e.g., Unwin, R. D., Griffiths, J. R., Leverentz, M. K., Grallert, A., Hagan, I. M. and Whetton, A. D. (2005) Multiple reaction monitoring to identify sites of protein phosphorylation with high sensitivity. *Mol Cell Proteomics* 4, 1134-1144, the entire content of which is incorporated herein by reference) to look for measurable tryptic peptides from a variety of plasma proteins. In this approach, the protein sequence is digested in silico, likely y-ion fragments are predicted, and theoretical MRM's generated for all the peptides in an acceptable size window. These MRM's are then used as a survey scan in a data dependent experiment to detect specific peptide peaks, and each resulting MRM peak is examined by full scan MS/MS to obtain sequence verification of the hypothesized peptide. From the full scan MS/MS data obtained, the most intense y-ion observed was used as the fragment ion for the MRM transition, this provides a further refinement over that predicted here in silico.

Random MRMs

Two approaches were used to generate pseudo-random MRM's for the present Example. In the first case, 100 MS1 values distributed randomly (by the Excel RAND function) between 408.5 and 1290.2 (the max and min of an early set of real MRM's were tested) were used and paired with MS2 values chosen randomly between this MS1 and the max of the real MRM's (1495.6), thus mimicking the properties of the real MRM's (which are generally +2 charge state peptides and +1 charge fragments). In a second set 131 MS1 values chosen randomly from among MS1 values in a large table of real MRM's were paired with MS2 values chosen randomly from the real MS2 values of the same list, imposing only the constraint that each MS2 had to be between 1 and 2 times the paired MS1 mass (to approximate our selection criteria for real MRM's).

Labeled Peptide Internal Standards: polySIS

A series of stable isotope labeled internal standard (SIS) peptides was added to samples in selected experiments by spiking with the tryptic digest of a polyprotein ("polySIS") to assess the performance of various embodiments of the methods of the present teachings and to provide a proof-of-concept for the assessment of the commercial potential of the methods. However, stable isotope peptides could come from any of a number of sources including, but not limited to, chemical synthesis of a peptide using an isotope labeled amino acid, and/or chemical labeling of synthetic peptides with labeling reagents (e.g., ICAT™, iTRAQ™). It is to be understood, however, that the use of a standard peptide in this example was for the purpose of assessing the methods of the present teachings and that a standard peptide is not required for use of the methods of the present teachings.

Briefly, this polySIS protein was produced by cell-free transcription and translation of a synthetic gene coding for 30 concatenated tryptic peptide sequences (derived from 30 plasma proteins) in the presence of U-$^{13}C_6$ U-$^{15}N_2$ labeled lysine (a total mass increment of 8 amu compared to the natural peptide). Of these peptides, 13 were used in the present studies (the remainder were not reproducibly detected with peak area>1e4). The positioning of the label atoms at the extreme c-terminus of each peptide has the effect that all fragments that contain the c-terminus (i.e., the y-ions) show the mass shift due to the label, whereas all the fragments that contain the n-terminus (and hence have lost one or more c-term residues: the b-series ions) have the same masses as the corresponding fragments from the natural (sample-derived) target protein. These features (shifted y-ions, normal b-ions) provide a simplification in interpreting the fragmentation patterns of the SIS peptides. To determine the absolute concentration of polySIS protein, an aliquot was diluted with 1M Urea, 0.05% SDS and 50 mM Tris, pH8 and subjected to N-terminal Edman sequencing, yielding an initial concentration of 5±1 picomole/µL. A tryptic digest of the polySIS protein was spiked into whole and depleted human plasma digests at the final concentrations as shown in Table 1.

Data Acquisition and Processing

Plasma digests with and without added polySIS standards were analyzed by electrospray LC-MS/MS using LC Packings (a division of Dionex, Sunnyvale Calif.) or Eksigent nanoflow LC systems (Table 1) with 75 micron diameter C18 PepMap reversed phase columns (LC Packings), and eluted with gradients of 3-30% acetonitrile with 0.1% formic acid. A column oven (Keystone Scientific, Inc.) was used to maintain the column temperature at 35° C. Electrospray MS data were collected using the NanoSpray® source on a 4000 Q TRAP hybrid triple-quadrupole/linear ion trap instrument (Applied Biosystems/MDS Sciex) and the peaks integrated using quantitation procedures in the Analyst software 1.4.1 (IntelliQuan algorithm). MRM transitions were acquired at unit resolution in both the Q1 and Q3 quadrupoles to maximize specificity.

MRM Transitions

In this Example, in an initial approach to the selection of representative peptides for MRM assays, a single peptide of 8 to 18 amino acids was chosen from each of 30 proteins spanning a broad range of plasma concentrations ($6.6\times10^8$ down to 1 fmol/ml normal concentration) based on computed characteristics alone (see, e.g., Anderson, N. L., Anderson, N. G., Haines, L. R., Hardie, D. B., Olafson, R. W. and Pearson, T. W. (2004) Mass spectrometric quantitation of peptides and proteins using stable isotope standards and capture by anti-peptide antibodies (siscapa). *J Proteome Res* 3, 235-44, the entire contents of which is incorporated herein by reference). MRM's were designed assuming doubly charged peptide ions, and using fragments selected as likely y-ions above the m/z of the 2+ parent ion, with collision energies assigned by a generic formula (CE=0.05*m/z+5) and the peptides expressed as a concatamer polySIS protein containing single copies of each peptide labeled with U-$^{13}C_6$ U-$^{15}N_2$ lysine. When a tryptic digest of the polySIS was analyzed, all 30 peptides were detected by MRM's. When a digest of whole human plasma was added to the polySIS peptides, 19 of the labeled polySIS peptides were detected by the same MRM's, but only 11 of the plasma digest-derived unlabeled cognate peptides were detected (by the same MRM's adjusted for isotope label masses).

Since different peptides from a single protein can vary widely in detectability by ESI-MS, an alternative approach to MRM design was also pursued based primarily on experimental data from a conventional peptide survey scan approach and applying the selection criteria to peptides with demonstrated detectability. Using a 3 hour LC gradient, MS/MS scans were collected for the major doubly or triply charged ions across the separation using information-dependent data acquisition (IDA), and a second run performed using time-filtered exclusions of the peptide ions detected in the first run. The combined results identified 54 plasma proteins, ranging in abundance from albumin down to fibronectin (normal plasma concentration of about 1 µg/ml). This experimental MS/MS data provided explicit information for peptide selection, charge state and most abundant y-ion m/z value under the specific conditions used (i.e., electrospray ionization with collisional peptide fragmentation), allowing improved design of MRMs. When these MRMs were then used to analyze the same sample in a subsequent run, triggering MS/MS scans at any MRM signal, most of the peptides were detected as peaks in the chromatogram and identified by database search. In most of these MRM chromatograms, only a single peak was detected.

Because peptide detection sensitivity using MRM is expected to be greater than that achieved in a full scan MS survey approach, a comprehensive de novo MRM design method was explored for those proteins not detected in the above survey experiment. Using an adaptation of a novel software tool, the MIDAS™ brand workflow (see above), a large set of MRM's was generated for each of a series of target proteins by selecting all predicted tryptic peptides in a useful size range, together with multiple high-mass y-ion fragments of each. These MRMs were then tested in LC-MS/MS runs of the unfractionated plasma digest, grouped in panels that included all the predicted tryptic peptides of one or two proteins at a time (50 to 100 MRMs per run), with MS/MS scans triggered on any peaks observed. Of 12 proteins examined, 9 produced at least one MRM with a signal-to-noise ratio (S/N) of greater than about 20. The obtained full scan MS/MS data was used to refine the MRM transition for improved detection in the final assay.

MRM results from the above approaches were pooled, and a set of optimized MRMs assembled that covered a total of 60 peptides representing 53 proteins in human plasma (see Table 2: seven proteins were represented by two peptides). This set includes 18 peptides selected by the in silico approach (8 of the initial 30 in silico peptides were eliminated as likely to be of too low abundance for detection, and better alternative peptides were selected from experimental data for 4 others). For all but one of the peptides, two fragments of the peptide (i.e., using two MRM's per peptide) were measured, yielding 119 MRM's. Finally MRM's for 18 stable isotope labeled internal standard ("SIS") versions of target peptides (i.e., the tryptic digest of the polySIS protein) spiked into the digest plasma samples were included. The resulting set of 137 MRM's was measured in all the replicate runs described in this Example, using a 18 msec dwell time per MRM, and a resulting cycle time of about 3 sec between measurements.

After the final MRM method was constructed, each MRM transition and respective retention time was validated again as indicative of each specific peptide. Full scan MS/MS was acquired upon the appearance of the MRM signal, and each resultant spectrum was manually inspected to determine matching to the specific peptide.

Discussion

An important component to the early and late stage validation of biomarkers in any body fluid is the ability to prepare and analyze many samples in parallel in a highly reproducible manner. In the present example, mass spectrometric MRM assays were designed from tryptic peptides representing 53 proteins in human plasma (see, Table 2, for a list of the proteins). In this Example, proteins down to about 1 μg/mL concentration in plasma, with minimal sample preparation, were reliably detected in both digested and depleted/digested human plasma, producing a dynamic range of about 5 orders of magnitude in this single method, as illustrated, for example, in FIG. 4B. Thus, in various embodiments, the present teachings can provide a robust platform for biomarker validation.

Six experimental sets (A-F) were performed. In each experiment, the same set of 137 MRM's was measured during sequential replicate LC-MS/MS runs of a single sample (same injection volume), and the appropriate peaks integrated using Analyst™ brand software to yield a value (peak area) for each MRM in each run. The reproducibility of the LC MRM method was assessed by measuring 10 LC-MRM replicates on the same sample. Experiments A-E (10 replicate runs each) are summarized in Table 1. These experiments included tryptic digests of both whole (unfractionated) human plasma (B,C) and plasma depleted of abundant proteins (A,D,E); high (B,E) and low (A,C,D) total peptide loadings; and different chromatographic setups. One objective of the experiments of this Example was to assess the performance of the MRM's in various typical plasma digest experiments. The reference peptide load (experiment A) was derived from tryptic digestion of the protein contained in 10 nL of plasma after subtraction of the most abundant proteins (about 80% of protein mass). This loading, comprising an estimated 60-70 ng of total peptides, proved to be a loading compatible with nanoflow chromatography of the MRM peptides. Experiments B and E used higher loadings to explore the tradeoff between peak stability (chromatographic quality, adversely affected by increased load) and signal-to-noise (S/N) ratio (improved by increased analyte quantity). In this Example, the loading of 60-70 ng, of the conditions investigated, was shown to be optimal. Chromatographic elution times were reproducible, showing, average CV's of 2% (experiment D) and 2.5% (experiment E).

Reproducibility Discussion

The reproducibility of both the depletion and digestion step of the plasma preparation was explored by both performing the sample preparation on aliquots of the same plasma samples on different days and by taking one sample, splitting it in two and performing parallel depletions, followed by a further split of each to perform parallel digestions on the same day. All samples were then assayed and correlated. The results suggest that these types of sample preparation techniques can be performed in a highly reproducible manner.

Reproducibility of Sample Preparation Across Disparate Preparations

Figure 10A:
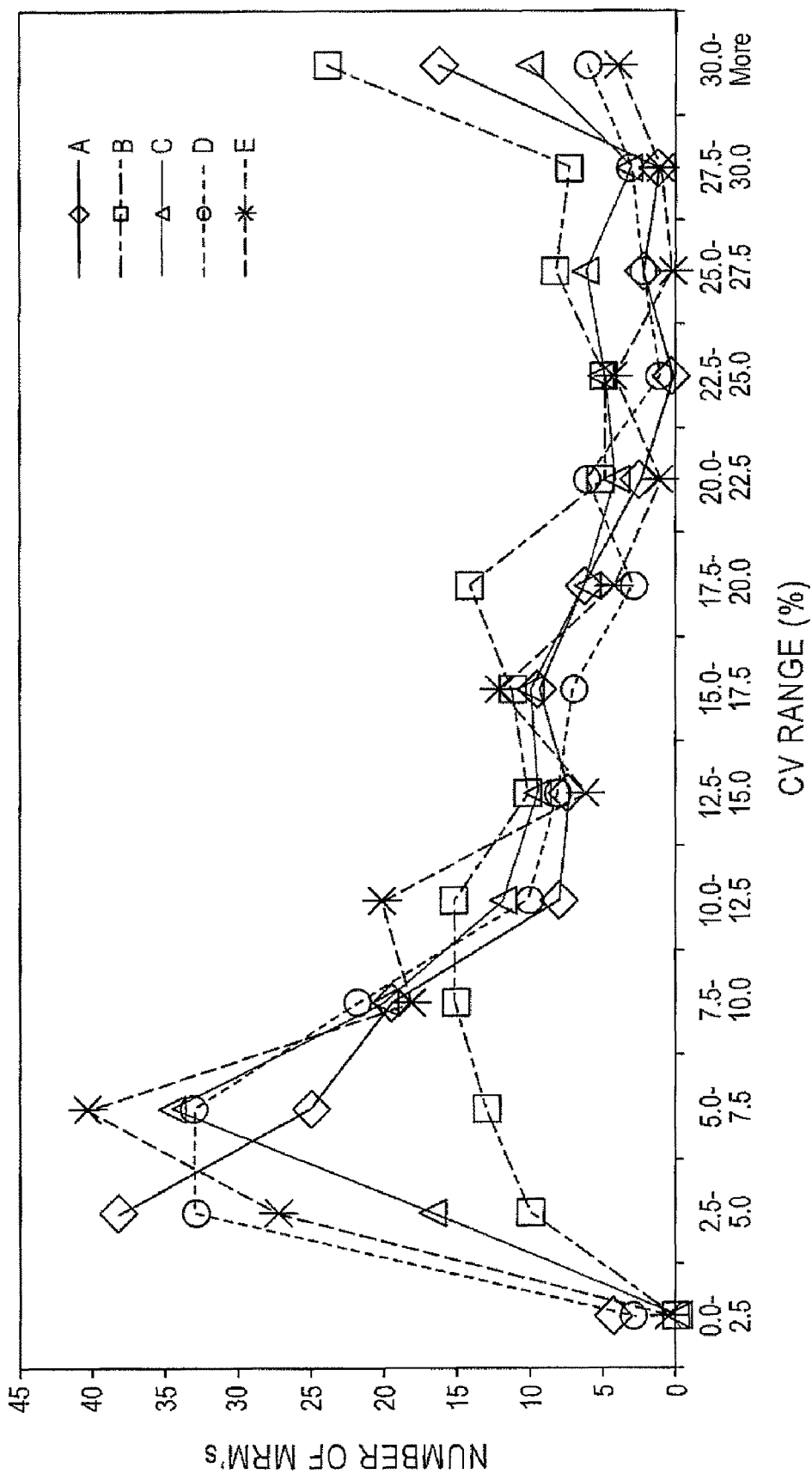
FIGS. 10A and 10B depict the distribution of CV values for five experimental sets of Example 2.
Figure 10B:
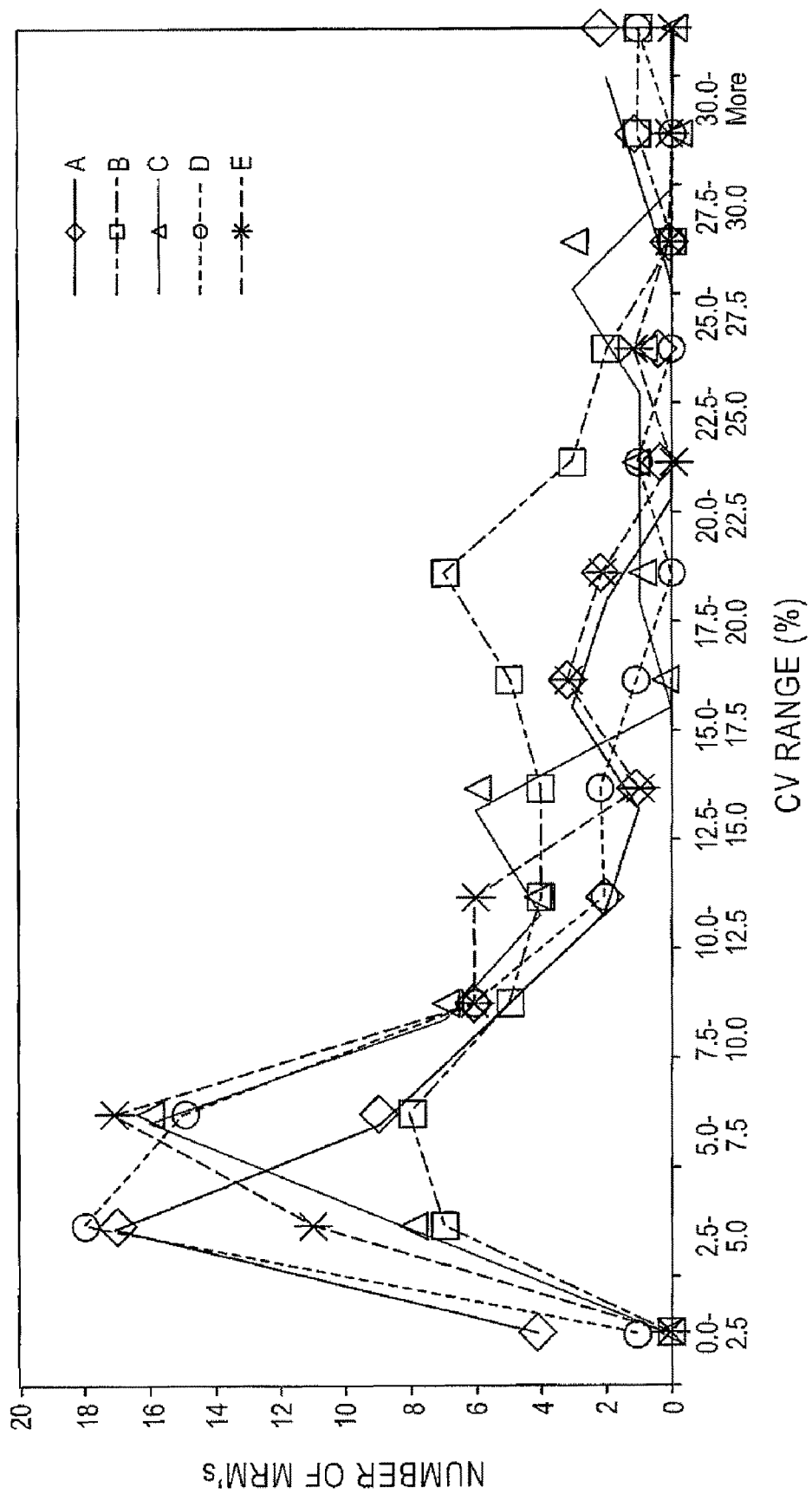

Referring to FIGS. 10A and 10B, FIG. 10A shows a histogram of CV's of MRM values (peak areas) for five experiments (A-E) across all 137 MRM's, such data was used to assess replicate reproducibility. The CV's were determined by performing 10 replicate injections on each sample, measuring the peak areas of each MRM transition, then calculating the average, standard deviation and coefficient of variation on each MRM across the 10 replicates. FIG. 10A shows histograms of the coefficients of variation (CV: standard deviation divided by mean peak area) for the 5 experiments (individual values for each MRM are presented in Table 2 which provides mean values and CV's for 10 replicate analysis across the 5 experiments). In the analyses of the depleted plasma, more than 60% of the MRM's shown within-run CV's of less than 10%, and almost half have CV's below 5%. A number of these MRM's (e.g., alpha-1-antichymotrypsin, apolipoprotein E, hemopexin, heparin cofactor II, plasminogen, prothrombin, fibrinogen gamma chain, complement C4 and factor B) showed an average within-run CV of 3-4% across three experiments, precision equivalent to that of typical good clinical immunoassays. Analyses of whole (undepleted) plasma digests showed generally higher CV's (20-50% of MRM's with CV<10%). These reproducibility measures were computed on raw peak areas, without correction using internal standards. Four of the measured proteins were expected to be removed by the protein immunodepletion process used. In comparing average peak areas obtained in analyses of digests of whole and depleted samples, substantial reductions in albumin (1.3e8 reduced to about 1e4), transferrin (1.5e5 reduced to about 5e3) and haptoglobin (4.6e6 reduced to about 1e5) were found. In this Example, alpha-1-antitrypsin was not detected with sufficient reliability to confirm its removal at this time in the analysis of the data.

Multiple measurements of an MRM would be expected to improve CV's, and thus the experiments also examined whether the sum of the two fragments measured separately for 59 of the peptides exhibited a smaller CV across 10 replicate runs than the individual MRM's. As shown in Table 3, the average CV for the summed MRM's across 59 peptides is 1-3% lower than the averages of either individual MRM. If the summed CV is compared to the lower of the two fragment CV's for each MRM, the average reduction in CV in experiments A-E ranges from +0.7% to −0.1%. These small improvements in CV come at the cost of doubling the measurement time (or halving the number of peptides monitored).

Figure 8:
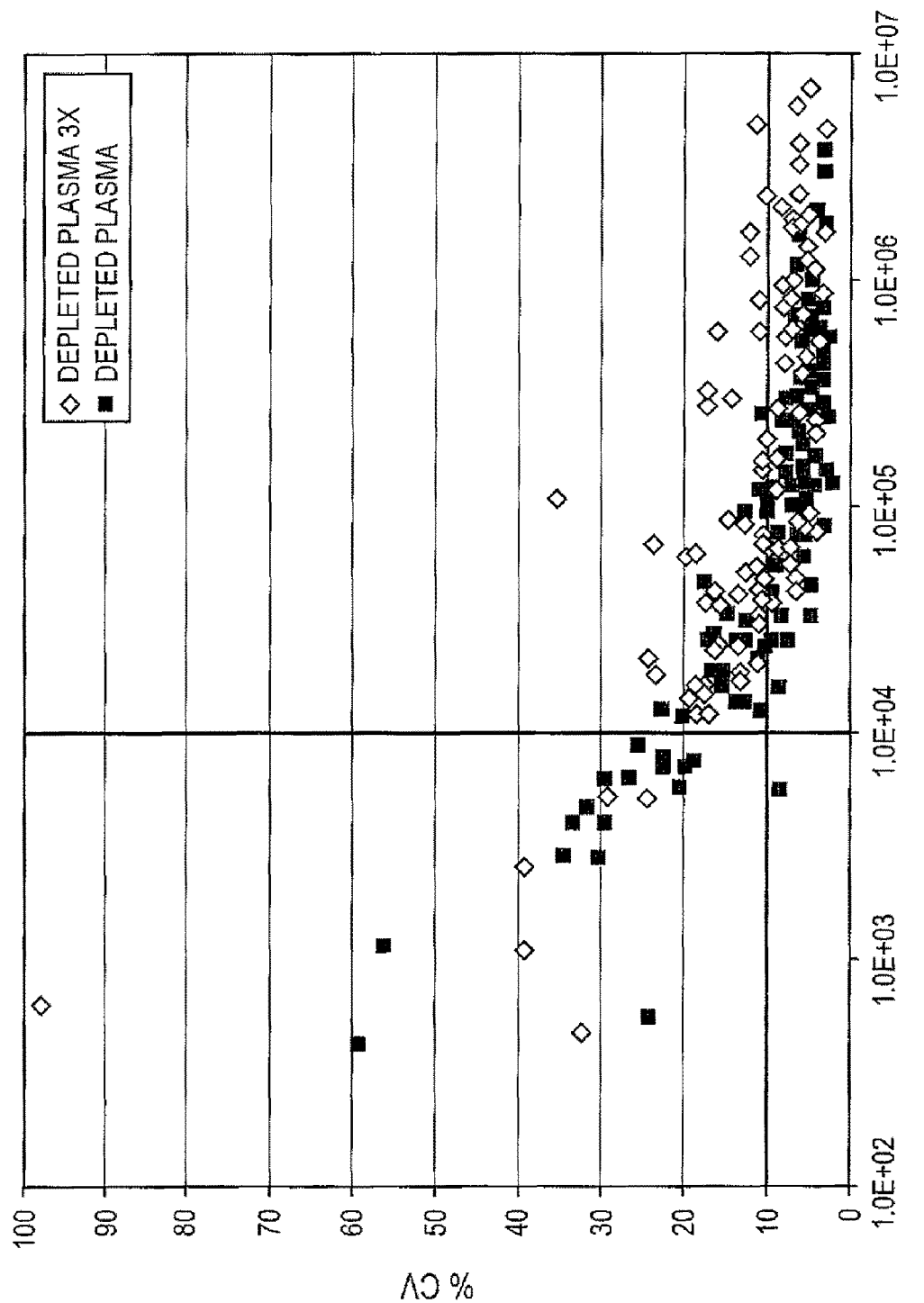
FIG. 8 is a plot of peak CV versus peak area for two experiments (digested plasma and depleted plasma) of Example 2.

The relationship between CV and peak area for experiments D and E, indicates at least for the data and conditions of this Example, that peak areas below 1e4 are unlikely to yield CV's below 10% (FIG. 8). A cutoff of 1e4 corresponds to a signal-to-noise ratio of about 10, which is consistent with the quantitative goal of a S/N of 10 for a reported lower limit of quantitation. The highest peak areas measured (albumin peptides in whole plasma digest samples) are above 1e8, demonstrating a maximal working dynamic range of greater than about 4 orders of magnitude above this cutoff.

Immunosubtraction Improves Reproducibility

Figure 9A:
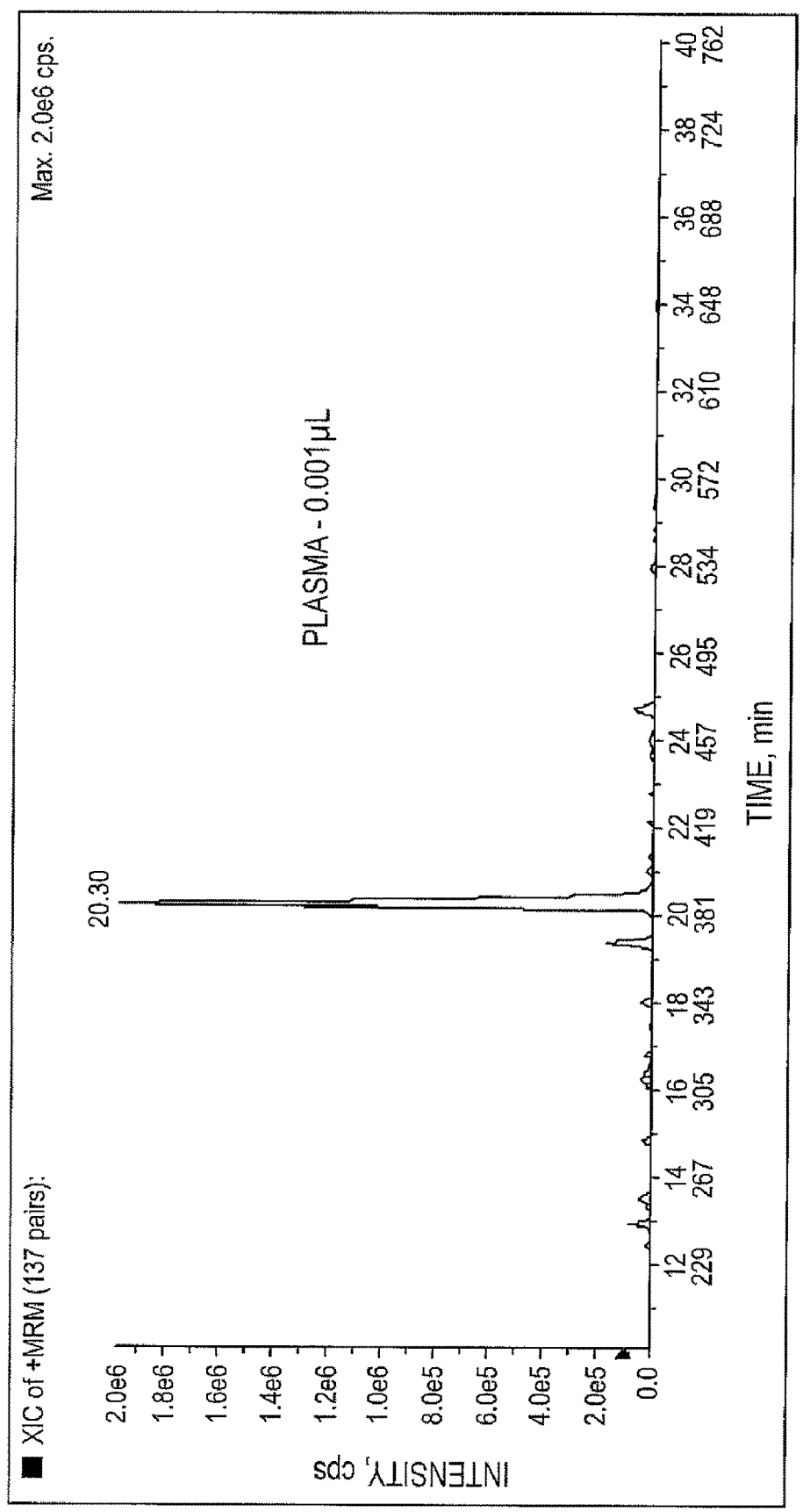
FIGS. 9A and 9B illustrate the effects of the depletion of the six most abundant proteins from plasma in Example 2.
Figure 9B:
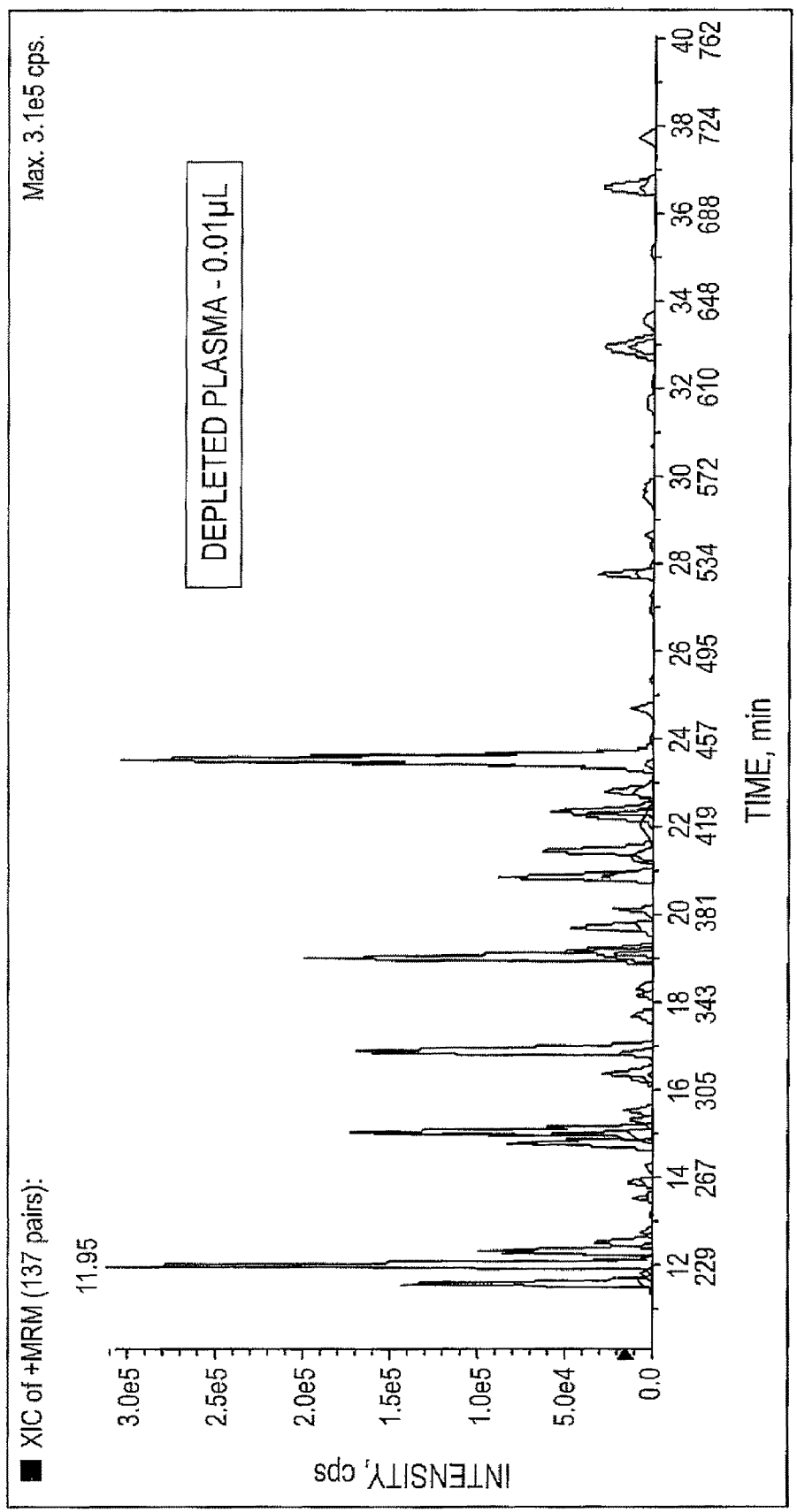

In general in this Example, immuno subtraction of the most abundant proteins using the Agilent MARS column improved the performance of MRM's for non-subtracted proteins. This effect, it is believed, is not simply due to improved detection sensitivity, since there were few if any peptides in the current set that were detected in depleted but not whole plasma digests. Rather the effect of depletion it is believed appears to be manifested in improved chromatographic peak shape achieved by decreasing the total peptide loaded by about 4-5-fold and in MRM peak signal-to-noise, both of which contribute to improved CV's. FIGS. 9A and 9B illustrate the benefit of depletion in removing the albumin peptide (major peak in FIG. 9A) and thus boosting the minor peaks in the depleted sample (FIG. 9B). At very high loading of undepleted plasma digest, large shifts in peak retention times were noticed, but at loadings in the region of the nominal load the effect of high abundance peptides on MRM retention times was minor.

Assessment of Reproducibility of Immunodepletion and Digest

Figure 5A:
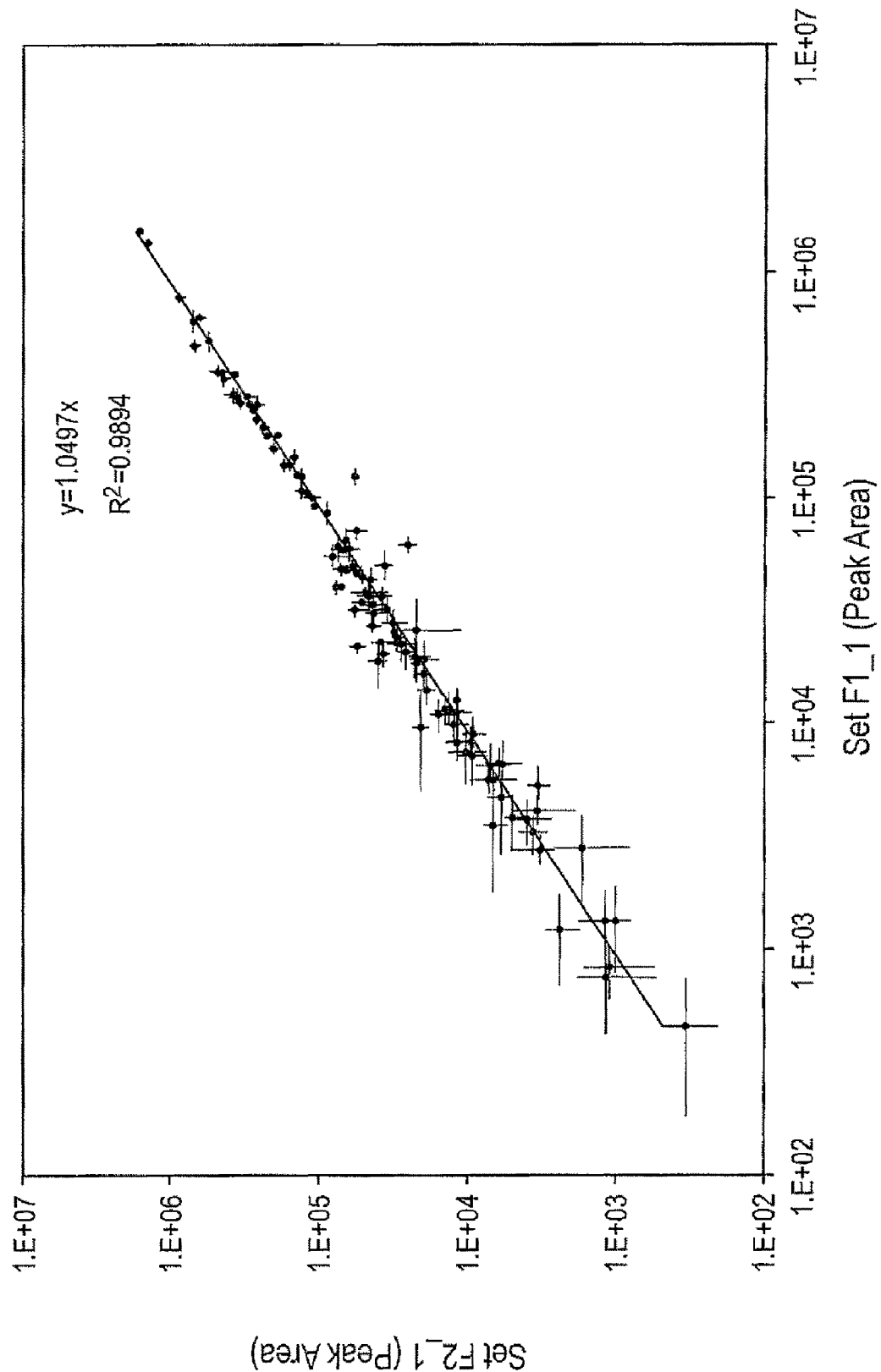
FIGS. 5A and 5B show correlation plots of peak areas of MRM transitions between a parallel depleted/digestion experiment and a parallel digestion experiment, respectively of Example 2 on the same plasma sample.
Figure 5B:
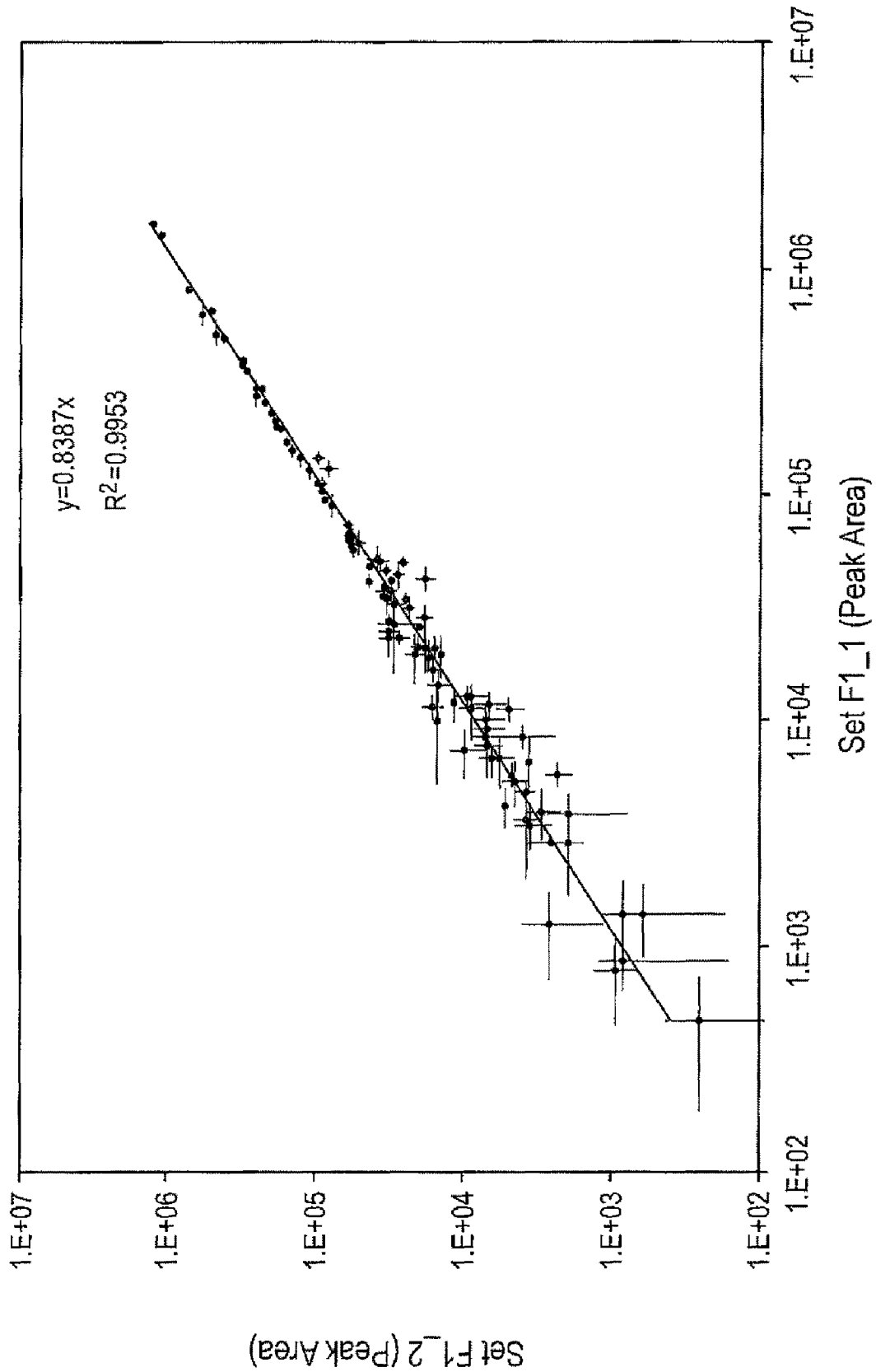

In a sixth experiment set (F series), MARS depletion on two aliquots of the same plasma sample was performed and then two aliquots of each depleted sample were separately digested (total of four samples; e.g., F1_2 refers to the second digest of the first depletion). Four replicate runs of the 137 MRM's were carried out for each sample in randomized order to avoid any sequence effect. FIGS. 5B and 5C compare the mean peak areas of two digests of a single depleted sample (FIG. 5C, F1__1 vs F1__2), two parallel depletion/digestions (FIG. 5B, F1__1 vs F2__1). Duplicate digests show excellent comparability ($R^2$=0.995 and 0.998 for F1__1 vs F1__2 and F2__1 vs F2__2 respectively). Duplicate depletions (which necessarily include the effects of different digests as well) are only slightly worse (e.g., $R^2$=0.989 and 0.991 for F2__1 vs F1__1 or F2__2 vs F1__2 respectively). (!!We need to rename 5B and C to 5A and B)

Assessment of Sensitivity

Two proteins with relatively low normal concentrations in plasma were unequivocally detected among the MRM's tested: L-selectin and fibronectin. The soluble form of L-selectin is a 33 kDa protein present in plasma at a normal concentration of about 0.67 µg/ml (26), or 20.3 pmol/ml. Fibronectin is a 260 kDa protein present in plasma at a normal concentration of about 1.4 µg/ml (27, (28), or 5.4 pmol/ml. Given that an amount of digest corresponding to 0.01 µl plasma was loaded on column in experiment D, these peptides would be expected to be present on column at about 200 and about 50 amol, respectively. In the case of L-selectin a spiked SIS standard at 2.0 fmol was used to determine that the natural (sample-derived) peptide was present at 0.1 times the amount of SIS (single point quantitation), yielding a measured 200 amol and implied plasma concentration of 0.6-0.67 µg/ml, in good agreement with expectation. CV's for fibronectin in runs D and E were 4% and 4% respectively, and for L-selectin 22% and 11% respectively, indicating that L-selectin was near the lower limit (~1e4) for high-quality detection in these experiments.

At the present time and stage of the analysis of the data, six of the 53 selected target proteins were not reliably observed. A reproducible signal for the selected peptides from coagulation factor V, vitamin K-dependent protein C, or C4b-binding protein were not obtained. There were also instances in which peptides from more abundant proteins were not reliably detected at the present time and stage of the analysis of the data. The inter-alpha trypsin inhibitor light chain (despite the fact that a peptide from the heavy chain of this protein gave a good quality MRM), apolipoprotein C-II, and alpha-1-antitrypsin was not reliably detected at this time. It is believed that an alternative choice of peptides for these more abundant proteins can lead to more reliable detection: numerous alternative peptides exist for both the inter-alpha trypsin inhibitor light chain and alpha-1-antitrypsin, but for small proteins, such as apolipoprotein C-II, there may be no better alternative and additional enrichment of these peptides in the sample loaded on the column would be indicated.

Behavior of Random MRMs and Density of MRM Signals

Most of the non-randomly designed MRM's appeared to detect only a single peak during the LC run of a complex digest such as depleted plasma: while 73% had a peak area greater than about 32,000 (approximating a signal-to-noise value of 10 in this data) corresponding to the target peptide analyte, only about 8% had a second peak meeting the same peak area criterion. Experiments, therefore, were attempted to confirm that the density of peptide peaks in "MRM-space" was indeed low (equivalent to high MS/MS detector specificity relative to sample complexity) by examining two types of randomized MRM's in the same depleted plasma digest sample. In a first set, 100 MRM's were generated with "parent" masses randomly distributed over the mass range of real peptides used in the 137 designed MRM's, and "fragment" masses randomly distributed between the "parent" mass and the maximum fragment mass among the designed MRM's ("random MRM's"). Of the 100 random MRM's, only 6 showed a peak with area greater than 32,000, and none of these peaks produced MS/MS spectra that led to a protein identification when searched with Mascot against SwissProt. A second set of 131 random MRM's was generated by randomly pairing parent ion and CID fragment ion masses from the set of designed MRM's detectable in plasma, excluding those cases where the fragment mass was lower than the parent ("random combination MRM's"). By using real peptide and fragment masses, these MRM's avoided potential bias arising from the tendency of real peptide masses to cluster around integral masses (the mass defect). In this second set, about 12% of the MRM's exhibited a peak with peak area greater than about 32,000, and none of these peaks gave MS/MS spectra yielding a protein identification. All the peaks observed in the random MRM sets occurred late in the LC gradient (after 100 min), after the elution of a large majority of the designed plasma protein MRM's. These results suggest that the density of quantifiable features in MRM-space at the current sensitivity of these experiments, even for a very complex peptide sample and using unit resolution in both mass analyzers, is only 6-12%, of which a minority may be canonical tryptic peptides. The distribution of peak areas observed for random MRM's closely matches the distribution for second (non-target peptide) peaks in the non-randomly designed MRM's, indicating that these additional peaks represent a random background.

Despite the complexity of plasma digests (particularly those of depleted plasma, where a small number of superabundant peptides have been removed), most MRM's exhibited only a single peak across the peptide LC chromatogram. This observation is consistent with the low density of peaks in two sets of randomly distributed MRM's measured in depleted plasma digests, and demonstrates the specificity of the two-stage QqQ-MS selection process used as the detector. The existence of secondary peaks (whether or not they are actually tryptic peptides) in a subset (about 10%) of MRM's indicates that chromatographic elution time may be a factor in providing the absolute analyte specificity desired in these assays.

Refinement of Predicted MRM Transitions

Approximately half of the peptides chosen by purely in silico means and used to create the PolySIS peptides (13 of 30) were detected in plasma and produced MS signals greater than about 1e4. Although the prediction of ionization properties of tryptic peptides can be expected to improve substantially in the future, in the present Example experimental MS/MS data was used to refine the predictions to select more better parent-daughter ion transitions. Two experimental methods proved particularly useful in the present Example. High abundance peptides were detected in conventional LC/MS/MS data dependent full-scan MS experiments, in which a subset of high-signal peptides seen in MS1 are subjected to MS/MS. Lower abundance peptides were detected by using the present teachings, by constructing lists of candidate MRM's to all appropriately-sized predicted tryptic peptides from a target protein, and then characterizing any detected MRM peaks by MS/MS (the MIDAS workflow, in which MRM methods are designed using a specifically-designed script within the Analyst™ brand software). Since MRM's are typically more sensitive than full scan survey MS for detection of very low abundance components, the MIDAS approach allowed us to improve MRM's (parent-daughter ion transitions) for more lower abundance peptides and, in various embodiments of the present teachings, this approach is used in the methods of developing a mass spectrometric based assay for a protein in a sample. This process was facilitated by the combination of high-sensitivity triple quadrupole MRM and ion trap MS/MS scan capabilities on the hybrid triple quadrupole linear ion trap 4000 Q TRAP mass spectrometer.

Figure 7A:
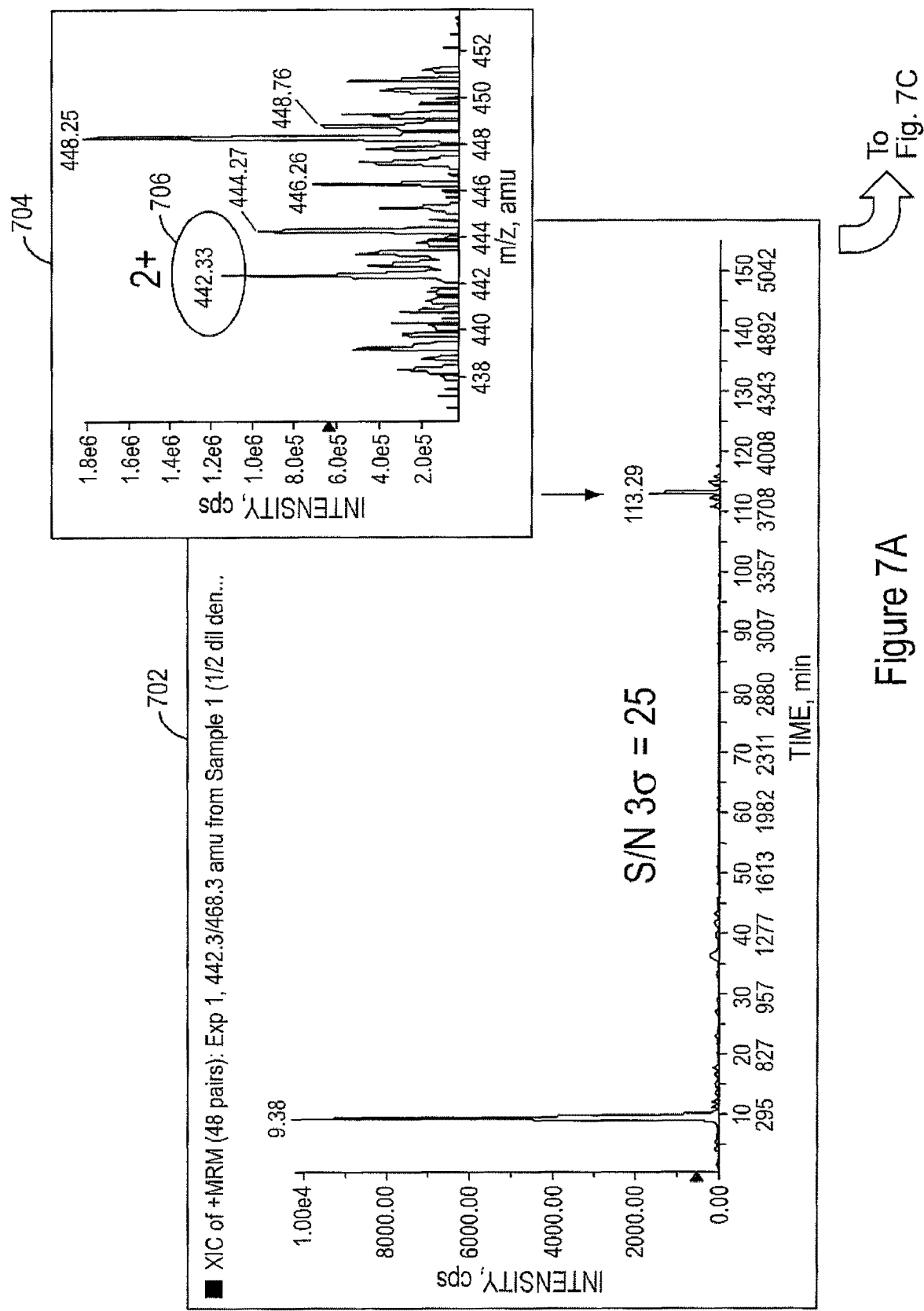
FIG. 7 schematically depicts refinement of predicted MRM transitions based on measured parent-daughter ion signals.
Figure 7B:
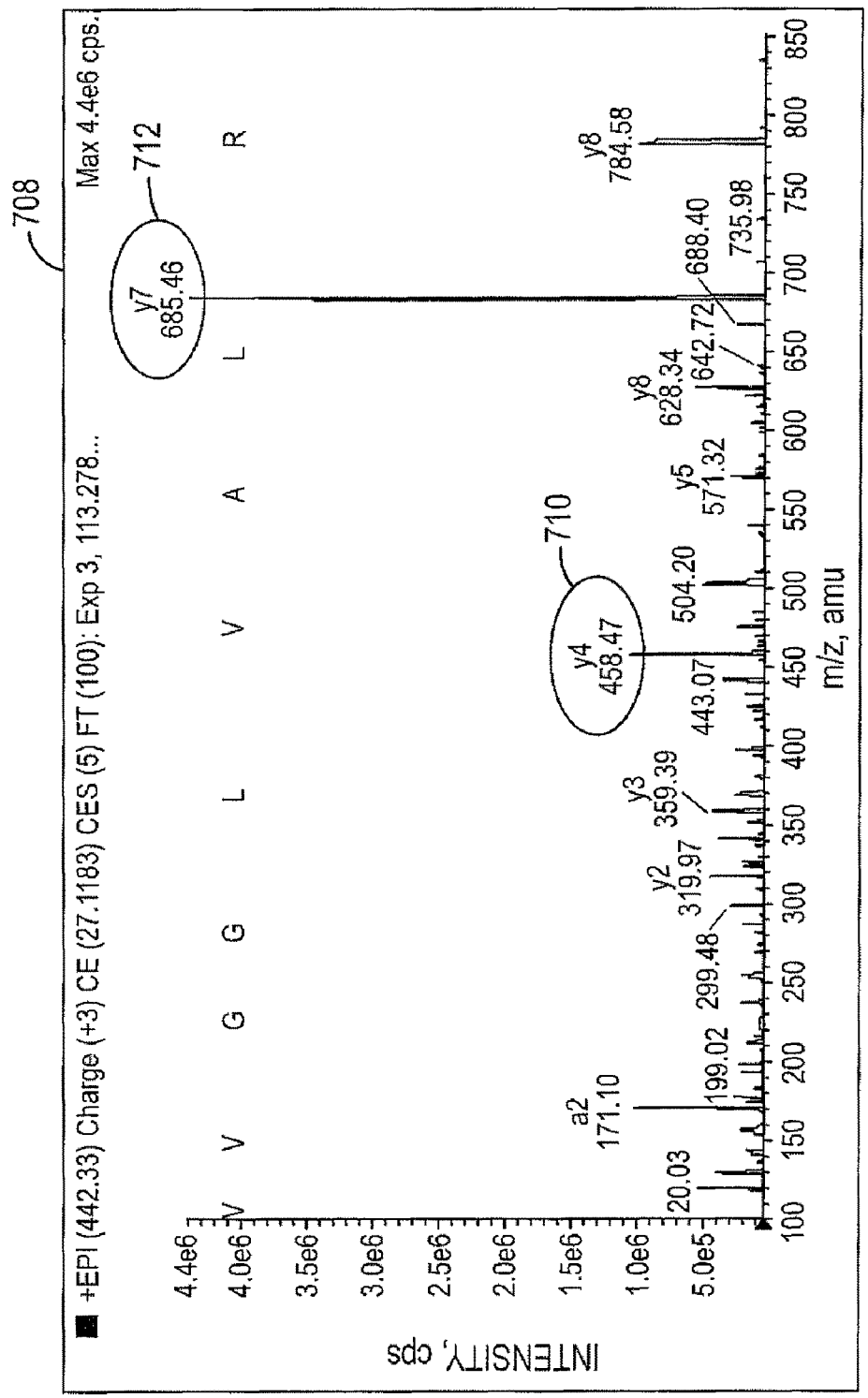
Figure 7C:
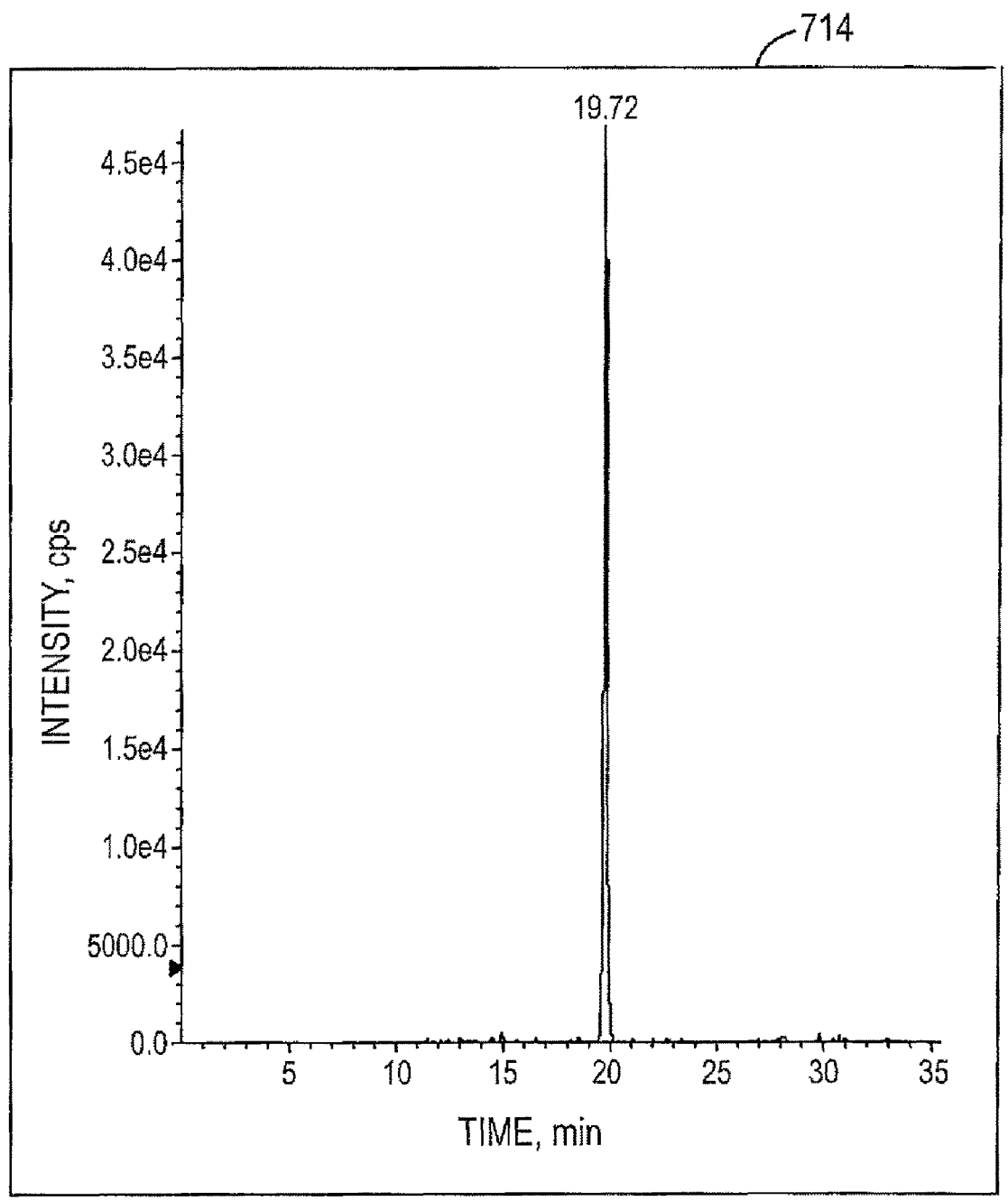

An example of this refinement approach is schematically illustrated in FIG. 7 for the protein coagulation factor XIIa light chain. Using the protein sequence from the SwissProt database for this protein, a list of 48 theoretical MRMs to 24 proteolytic peptides was generated and used as a survey scan. As an example, one of these MRMs is shown 702 and subsequent enhanced resolution scan 704 were conducted using in silico predicted parent-daughter ion transitions. Signal due to the predicted peptide was observed 706. A full product ion scan 708 revealed that the predicted daughter ion 710 had substantially less signal intensity than another fragment 712. The information from this scan 708 was used to refine the predicted MRM (parent-daughter ion) transition, and a new MRM was obtained 714 with higher signal-to-noise than the original MRM 702. This refinement process was done for two proteolytic peptides from this protein, but just one peptide was chosen for the final assay, based on its superior signal intensity and S/N.

Selection of a Parent-Daughter Ion Transition (MRM) for an Assay of a Protein

The parent-daughter ion transition (MRM) were identified from the 119 tested MRM's as possessing desirable properties for an assay for the respective protein is indicated by an "X" in the column "Best MRM" in Table 2. For 59 cases the fragment (daughter) ions were selected from two tested fragment ions; and for 7 cases the peptides (proteolytic fragment) were selected from cases where two peptides were tested per protein. Each of the 47 peptide sequences (of the 47 MRM assays) was verified as unique in the human proteome (represented by the Ensemble peptides), and occurred only once in the target protein. Three of the peptides (representing antithrombin III, apolipoprotein E and vitamin K-dependent protein C) occur in the mouse as well, and seven (apolipoprotein E and vitamin K-dependent protein C, complement C4 beta and gamma, fibronectin, haptoglobin beta, and inter-alpha trypsin inhibitor heavy chain) occur in the rat (all the other human sequences did not occur in the other species' Ensemble peptides).

Of the final 47 MRM assays, 12 were contributed by the in silico approach leading to the 30 polySIS peptides and one (hemopexin) by an earlier in silico effort (see, g.e., Anderson, N. L., Anderson, N. G., Haines, L. R., Hardie, D. B., Olafson, R. W. and Pearson, T. W. (2004) Mass spectrometric quantitation of peptides and proteins using stable isotope standards and capture by anti-peptide antibodies (siscapa). *J Proteome Res* 3, 235-44, the entire contents of which are hereby incorporated by reference). A total of 8 in silico selections were replaced by peptides from the same target protein as a result of experimental testing (4 before and 4 after selection of the 137 MRM's), 2 subsequently failed and have not yet been replaced, and 8 were dropped before testing because of expected insufficient abundance. Thus 13 in silico selections survived, while 10 were replaced in testing. The distribution of CV's for the 47 best MRM's across the five experiments (A-E) is shown in FIG. 10B, e.g., in experiment D, 40 of these had CV's below 10% and 19 below 5%, illustrating the potential of this method for reproducible quantitation.

One or more MRM transitions can then be selected as the parent-daughter ion transition for an assay of the presence of the protein in the biological sample (human plasma) were selected based on (i) the peptide (parent) of the parent-daughter ion transition was a verified as a proteolytic fragment of said protein based on a full product ion scan of the peptide, and at least one of the following properties, (ii) the selected parent-daughter ion transition had, relative to the measured ion signals associated with the other parent-daughter ion transitions for the protein, the approximately highest ion signal (as determined by peak are in this Example); (iii) the selected parent-daughter ion transition had, relative to the measured ion signals associated with the other parent-daughter ion transitions for the protein, the approximately highest signal-to-noise ratio; and/or (iv) the selected parent-daughter ion transition had, relative to the measured ion signals associated with the other parent-daughter ion transitions for the protein, the ion signal with the approximately smallest amount of error in the ion signal (e.g., MRM chromatogram peaks isolated from other peaks and/or appearing in areas of low background typically have lower errors in the ion signal value when determined by peak area relative to peaks which are in regions of high background and/or overlap with other peaks).

Multiplexing and Throughput Discussion

The multiplexing capability of LC-QqQ-MS platforms for measuring peptides in complex digests can be substantial, providing an opportunity to measure large panels of proteins accurately in each run. Based on the performance of the present set of 137 MRM's, which were all monitored continuously across the entire LC gradient as 18 msec sequential measurements, 100-200 MRM's might be used routinely to measure peptides in long LC gradients. Given reproducible chromatographic elution times, it is possible with existing systems to measure each MRM during a time window (e.g., static, dynamic, or combinations thereof) when the peak is expected to occur (e.g., a window of 10% of total run length, given an average 2-2.5% CV in peak elution time measured in our experiments D and E). Based on knowledge of elution time and column reproducibility, and selection of MRM's do not cluster too much in elution time, 10-fold more MRM's (1,000-2,000) could potentially be employed in a single LC MRM experiment.

An additional consideration for throughput of MRM measurements is the duration of the chromatography run. In replicate experiments D and E, a 30 min gradient was used, which led to a total cycle time (including inter-sample wash) of 75 min. The analyte specificity indicated by the low density of peaks in MRM-space indicates that, in various embodiments, suitable MRM's for protein assays can be developed with less benefit from chromatographic separation. The ability to focus MRM measurements in discrete time windows can allow more MRM's to be brought closer together in elution time used without sacrificing the required multiple measurements across each peak. In various embodiments, improvements in run time can be obtained in conjunction with a shift to higher flowrate (e.g., capillary flow) systems to facilitate providing, e.g., increased robustness in routine operation.

Example 3

Assessment of Quantitation Using an Internal Standard Peptide

Figure 6A:
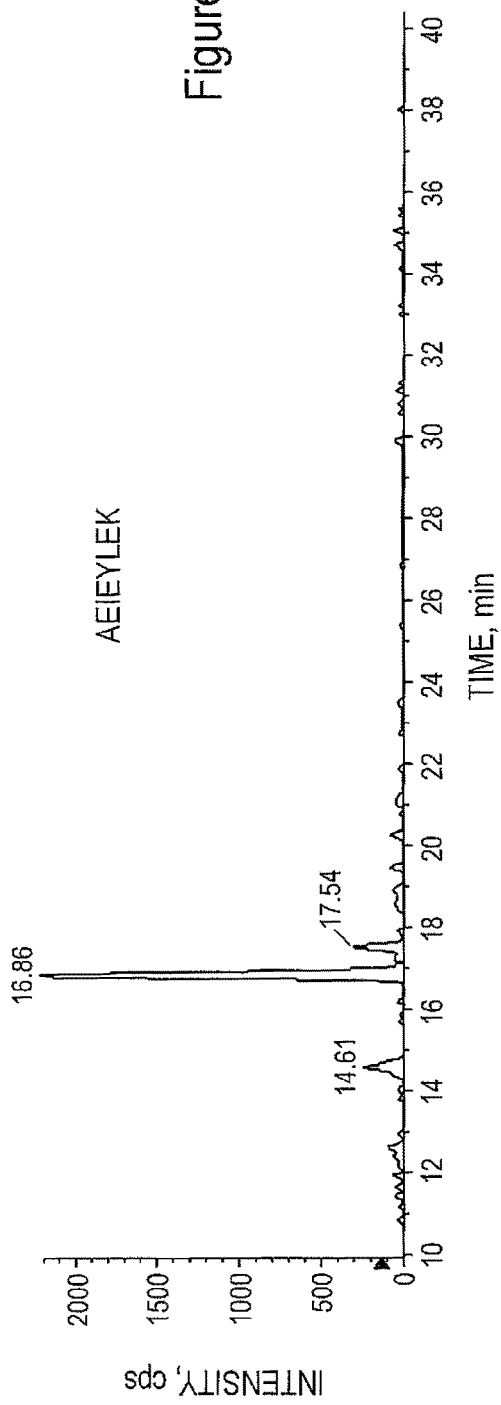
FIGS. 6A and 6B compare MRM data of Example 3 for a peptide fragment of L-selectin from the sample, FIG. 6A, to that for an isotope labeled synthetic peptide FIG. 6B.
Figure 6B:
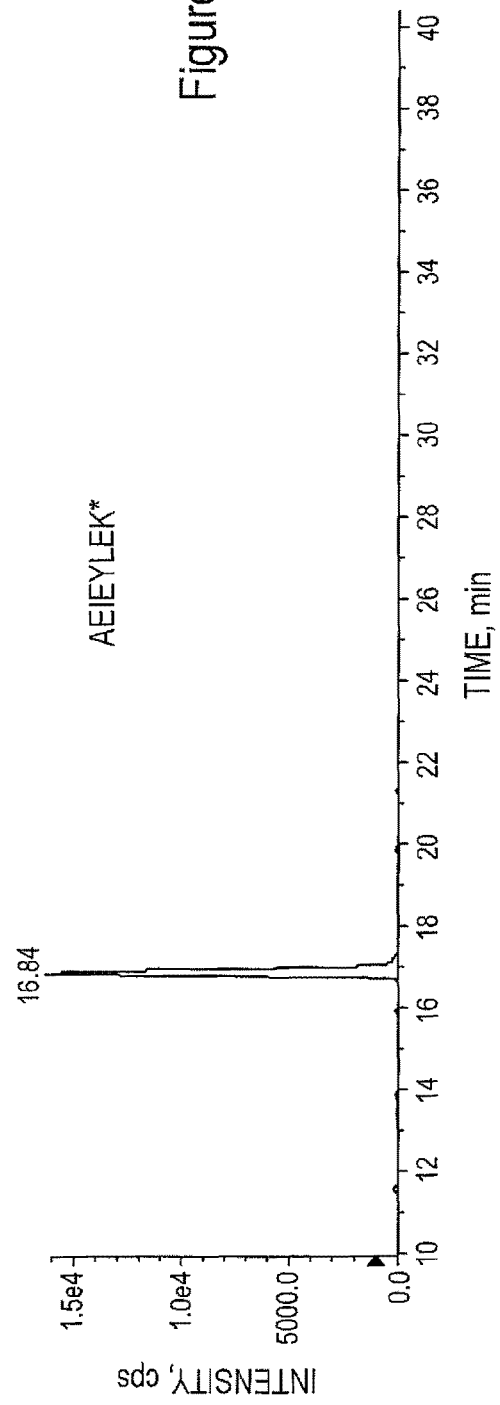

Stable isotope labeled peptides can be included, although not required, in the methods of the present teachings to provide an internal standard for absolute protein quantitation in the final assay. In the initial assay, the peptides were added at a known amount and used as a reference against which to measure the amount of the corresponding protein in plasma. A single point concentration curve was generated: more accurate quantitation can be provided a multiple point concentration curve. As an example, FIGS. 6A and 6B shows the comparative MRM data for the proteolytic peptide fragment AEIEYLEK from L-selectin, FIG. 6A, and that for an isotopically labeled fragment AEIEYLEK* of the standard. Using the ratios of the areas of the labeled (FIG. 6B) and unlabeled peaks (FIG. 6A) and the known labeled L-selectin peptide concentration (2 fmol on column), the plasma concentration of L-selectin was determined to be about 0.7 µg/mL, in good agreement with the literature value for this protein of 0.67 µg/mL.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the assays of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

TABLE 1

Summary of Data Sets for Experiments A-F

| Experiment | eps | Sample | LC system | Equivalent Plasma Volume Loaded (µL) | Load factor - total protein | Load factor - non-depleted proteins | PolySIS spike (fmol) |
|---|---|---|---|---|---|---|---|
| A | 10 | Depleted plasma digest | LC Packings | 0.01 | 1 | 1 | 1.3 |
| B | 10 | Whole plasma digest | LC Packings | 0.01 | 10 | 1 | 1.3 |
| C | 10 | Whole plasma digest | Eksigent | 0.001 | 1 | 0.1 | 2.0 |
| D | 10 | Depleted plasma digest | Eksigent | 0.01 | 1 | 1 | 2.0 |
| E | 10 | Depleted plasma digest | Eksigent | 0.033 | 3.3 | 3.3 | 6.0 |
| F1_1 | 4 | Depletion 1, digest 1 | Eksigent | 0.01 | 1 | 1 | — |
| F1_2 | 4 | Depletion 1, digest 2 | Eksigent | 0.01 | 1 | 1 | — |
| F2_1 | 4 | Depletion 2, digest 1 | Eksigent | 0.01 | 1 | 1 | — |
| F2_2 | 4 | Depletion 2, digest 2 | Eksigent | 0.01 | 1 | 1 | — |

Replicate runs were performed with 30 minute washes between. Load is expressed as the equivalent volume of plasma from which the sample was derived.

TABLE 2

MRM Count

| Protein | Peptide Sequence | RT in D | Best MRM | SIS | MS1/MS2 | Mean Peak Areas A | B |
|---|---|---|---|---|---|---|---|
| Afamin | DADPDTFFAK | 1.5 | X | | 563.8/825.4 | 1.7E+05 | 2.0E+05 |
| | | | | | 563.8/940.4 | 3.8E+04 | 5.9E+03 |
| Alpha-1-acid glycoprotein 1 | NWGLSVYADKPETTK | 9.7 | | | 570.3/1052.5 | 2.3E+05 | 5.9E+04 |
| | | | X | | 570.3/575.3 | 3.9E+05 | 9.7E+04 |
| | | | | X | 575.6/1068.5 | 1.4E+04 | 2.3E+04 |
| Alpha-1-antichymotrypsin | EIGELYLPK | 2.4 | | | 531.3/633.4 | 5.0E+05 | 1.2E+05 |
| | | | X | | 531.3/819.5 | 7.5E+05 | 1.6E+05 |
| | | | | X | 535.3/827.5 | 4.7E+04 | 1.6E+05 |
| Alpha-1B-glycoprotein | LETPDFQLFK | 7.7 | | | 619.4/995.5 | 2.1E+05 | 2.7E+04 |
| | | | X | | 619.4/894.5 | 5.2E+05 | 7.3E+04 |
| Alpha-2-antiplasmin | LGNQEPGGQTALK | 2.6 | X | | 656.8/771.4 | 3.5E+05 | 7.8E+04 |
| | | | | | 656.8/900.5 | 3.7E+04 | 7.1E+03 |
| | | | | X | 660.8/779.4 | 1.8E+05 | 5.1E+05 |
| Alpha-1-antitrypsin | DTEEEDFHVDQVTTVK | 7.4 | | | 631.3/790.4 | 8.5E+03 | 2.9E+03 |
| | | | | | 631.3/889.5 | 1.3E+04 | 3.5E+03 |
| Alpha-2-macroglobulin | LLIYAVLPTGDVIGDSAK | 6.5 | X | | 923.0/1059.5 | 4.1E+05 | 5.3E+04 |
| | | | | | 923.0/1172.5 | 1.5E+05 | 1.9E+04 |
| Angiotensinogen | ALQDQLVLVAAK | 3.5 | | | 634.9/956.6 | 3.3E+04 | 1.6E+04 |
| | | | | | 634.9/713.5 | 3.8E+04 | 2.0E+04 |
| | | | | X | 638.9/964.6 | 2.7E+04 | 7.3E+04 |
| | PKDPTFIPAPIQAK | 9.1 | | | 508.3/724.4 | 2.8E+04 | 3.3E+04 |
| | | | X | | 508.3/556.4 | 3.0E+04 | 1.2E+05 |
| Antithrombin-III | DDLYVSDAFHK | 9.2 | | | 437.2/803.4 | 9.1E+04 | 2.1E+04 |
| | | | X | | 437.2/704.3 | 3.3E+05 | 7.5E+04 |
| | | | | X | 439.9/811.4 | 4.5E+03 | 1.3E+04 |

TABLE 2-continued

| Protein | Peptide | | | | m/z | | |
|---|---|---|---|---|---|---|---|
| Apolipoprotein A-I | ATEHLSTLSEK | 2.1 | X | | 405.9/664.4 | 2.1E+06 | 4.8E+05 |
| | | | | | 405.9/777.5 | 1.9E+06 | 4.0E+05 |
| | | 2.1 | | X | 408.5/672.4 | 2.2E+04 | 5.4E+04 |
| Apolipoprotein A-II precursor | SPELQAEAK | 2.1 | | | 486.8/546.4 | 5.3E+05 | 2.9E+05 |
| | | | X | | 486.8/659.4 | 8.3E+05 | 5.4E+05 |
| Apolipoprotein A-IV | SLAPYAQDTQEK | 3.8 | X | | 675.8/982.4 | 7.4E+04 | 1.8E+04 |
| | | | | | 675.8/1079.5 | 1.8E+05 | 3.6E+04 |
| Apolipoprotein B-100 | FPEVDVLTK | 2.8 | | | 524.3/803.5 | 5.1E+04 | 6.8E+04 |
| | | | X | | 524.3/674.4 | 4.7E+04 | 5.8E+04 |
| | | | | X | 528.3/811.5 | 7.1E+04 | 2.7E+05 |
| | TEVIPPLIENR | 2.9 | | | 640.8/838.4 | 6.4E+05 | 1.5E+05 |
| | | | | | 640.8/741.4 | 1.6E+05 | 3.6E+04 |
| Apolipoprotein C-I lipoprotein | TPDVSSALDK | 4.9 | X | | 516.8/620.3 | 1.8E+04 | 7.2E+03 |
| | | | | | 516.8/719.4 | 1.3E+04 | 4.8E+03 |
| Apolipoprotein C-II lipoprotein | STAAMSTYTGIFTDQVLSVLK | 6.2 | | | 745.1/1149.7 | 2.0E+04 | 4.4E+03 |
| | | 5.4 | | | 745.1/1002.6 | 1.9E+03 | 2.5E+03 |
| Apolipoprotein C-III | DALSSVQESQVAQQAR | 7.8 | | | 858.9/1144.6 | 1.0E+05 | 9.5E+04 |
| | | | X | | 858.9/1417.7 | 1.7E+04 | 1.7E+04 |
| Apolipoprotein E | LGPLVEQGR | 5.5 | | | 484.8/701.4 | 5.6E+04 | 2.5E+04 |
| | | | X | | 484.8/588.3 | 1.6E+05 | 5.5E+04 |
| Beta-2-glycoprotein I | ATVVYQGER | 2.4 | | | 511.8/652.3 | 7.4E+05 | 1.6E+05 |
| | | | X | | 511.8/751.4 | 6.7E+05 | 1.5E+05 |
| | EHSSLAFWK | 9.3 | | | 552.8/838.5 | 3.0E+04 | 3.2E+03 |
| | | | | | 552.8/664.4 | 6.1E+03 | 1.2E+03 |
| | | | | X | 556.8/846.5 | 4.6E+03 | 8.0E+03 |
| C4b-binding protein alpha chain | LSLEIEQLELQR | 7.0 | | | 735.9/915.5 | 1.2E+04 | 2.2E+03 |
| | | | | | 735.9/1028.6 | 9.7E+03 | 2.0E+03 |
| Ceruloplasmin | EYTDASFTNR | 4.9 | | | 602.3/624.3 | 3.5E+05 | 7.8E+04 |
| | | | X | | 602.3/695.3 | 3.0E+05 | 6.7E+04 |
| Clusterin | LFDSDPITVTVPVEVSR | 8.5 | | | 937.5/1296.7 | 1.5E+05 | 3.2E+04 |
| | | | X | | 937.5/686.4 | 3.1E+05 | 6.8E+04 |
| Coagulation factor V | DPPSDLLLLK | 6.7 | | | 555.8/898.6 | 8.1E+03 | 1.8E+03 |
| | | | X | | 559.8/906.6 | 2.0E+04 | 6.8E+04 |
| Coagulation factor XIIa light chain | VVGGLVALR | 9.7 | | | 442.3/784.5 | 2.6E+04 | 6.3E+03 |
| | | | X | | 442.3/685.4 | 3.2E+05 | 8.0E+04 |
| Complement C3 | TGLQEVEVK | 5.0 | | | 501.8/731.4 | 1.7E+06 | 3.8E+05 |
| | | | X | | 501.8/603.3 | 1.3E+06 | 2.9E+05 |
| | | | | X | 505.8/739.4 | 1.7E+04 | 5.6E+04 |
| Complement C4 gamma chain | ITQVLHFTK | 6.2 | | | 362.9/645.4 | 1.1E+05 | 2.6E+04 |
| | | | X | | 362.9/744.4 | 1.2E+05 | 3.2E+04 |
| | | | | X | 365.6/653.4 | 1.3E+04 | 4.8E+04 |
| Complement C4 beta chain | VGDTLNLNLR | 0.9 | X | | 557.8/629.4 | 8.9E+05 | 1.9E+05 |
| | | | | | 557.8/843.5 | 3.0E+05 | 6.5E+04 |
| Complement C9 | AIEDYINEFSVR | 8.3 | X | | 728.5/1271.6 | 5.2E+04 | 9.6E+03 |
| | | | | | 728.5/1027.5 | 3.0E+04 | 6.1E+03 |
| Complement factor B | EELLPAQDIK | 9.0 | X | | 578.4/671.4 | 1.9E+06 | 3.3E+05 |
| | | | | | 578.4/784.5 | 2.7E+05 | 4.5E+04 |
| Complement factor H | SPDVINGSPISQK | 6.3 | X | | 671.4/830.4 | 7.2E+04 | 1.2E+04 |
| | | | | | 671.4/572.3 | 4.4E+04 | 8.5E+03 |
| Fibrinogen alpha chain | TVIGPDGHK | 1.7 | | | 462.3/723.4 | 4.4E+03 | 2.2E+05 |
| | | | | | 462.3/610.3 | 1.0E+03 | 1.7E+05 |
| | | | | X | 466.2/731.4 | 2.8E+03 | 1.0E+05 |
| | GSESGIFTNTK | 4.7 | X | | 570.8/780.4 | 1.0E+06 | 2.3E+05 |
| | | | | | 570.8/867.5 | 1.1E+06 | 2.2E+05 |
| Fibrinogen beta chain | QGFGNVATNTDGK | 3.5 | X | | 654.8/706.3 | 2.1E+06 | 3.4E+05 |
| | | | | | 654.8/805.4 | 6.2E+05 | 9.8E+04 |
| | | | | X | 658.8/714.3 | 6.1E+04 | 1.4E+05 |
| Fibrinogen gamma chain | DTVQIHDITGK | 5.4 | | | 409.5/670.4 | 2.7E+05 | 7.1E+04 |
| | | | X | | 409.5/533.3 | 2.6E+05 | 7.6E+04 |
| | | | | X | 412.2/678.4 | 2.3E+04 | 5.5E+04 |
| Fibronectin | DLQFVEVTDVK | 4.7 | X | | 647.3/789.4 | 7.4E+04 | 2.9E+04 |
| | | | | | 647.3/690.4 | 1.0E+05 | 3.6E+04 |
| | VTWAPPPSIDLTNFLVR | 8.2 | | | 642.7/977.5 | 1.4E+04 | 4.5E+03 |
| | | | | | 642.7/862.5 | 9.6E+03 | 3.7E+03 |
| Gelsolin, isoform 1 | TGAQELLR | 4.8 | X | | 444.3/786.5 | 1.1E+05 | 2.7E+04 |
| | | | | | 444.3/729.4 | 1.5E+05 | 3.5E+04 |
| Haptoglobin beta chain | VGYVSGWGR | 8.2 | X | | 490.8/562.3 | 4.2E+05 | 1.6E+06 |
| | | | | | 490.8/661.3 | 2.0E+05 | 8.1E+05 |
| Hemopexin | NFPSPVDAAFR | 3.6 | X | | 610.8/959.6 | 4.9E+06 | 8.8E+05 |
| | | | | | 610.8/775.3 | 3.3E+06 | 7.1E+05 |
| Heparin cofactor II | TLEAQLTPR | 6.4 | X | | 514.8/814.4 | 3.3E+05 | 9.0E+04 |
| | | | | | 514.8/685.4 | 2.9E+05 | 7.0E+04 |
| Histidine-rich glycoprotein | DSPVLIDFFEDTER | 7.7 | X | | 841.9/1171.5 | 7.7E+04 | 2.9E+04 |
| | | | | | 841.9/1058.4 | 7.3E+04 | 2.9E+04 |
| Inter-alpha-trypsin inhibitor heavy chain | AAISGENAGLVR | 4.9 | X | | 579.4/902.5 | 6.3E+05 | 1.7E+05 |
| | | | | | 579.4/629.4 | 1.7E+05 | 4.4E+04 |
| Inter-alpha-trypsin inhibitor light | AFIQLWAFDAVK | 8.0 | | | 704.9/836.4 | 3.0E+04 | 5.3E+03 |
| | | | | | 704.9/949.5 | 1.5E+04 | 2.9E+03 |
| Kininogen | TVGSDTFYSFK | 1.5 | X | | 626.3/1051.4 | 8.7E+05 | 1.5E+05 |
| | | | | | 626.3/994.5 | 8.7E+04 | 1.4E+04 |

TABLE 2-continued

| Protein | Peptide Sequence | | | | | | |
|---|---|---|---|---|---|---|---|
| L-selectin | AEIEYLEK | 6.9 | | | 497.8/794.4 | 1.9E+04 | 6.0E+03 |
| | | | X | | 497.8/681.3 | 1.2E+04 | 3.4E+03 |
| | | | | X | 501.8/802.4 | 8.4E+04 | 3.0E+05 |
| Plasma retinol-binding protein precursor | YWGVASFLQK | 5.1 | X | | 599.8/849.5 | 9.5E+04 | 1.1E+04 |
| | | | | | 599.8/693.4 | 5.9E+04 | 7.1E+03 |
| Plasminogen | LSSPAVITDK | 5.3 | | | 515.8/743.4 | 1.8E+05 | 8.8E+04 |
| | | | | | 515.8/830.5 | 1.2E+05 | 5.4E+04 |
| | | | | X | 519.8/751.4 | 8.6E+04 | 3.0E+05 |
| | LFLEPTR | 9.1 | | | 438.3/615.4 | 5.3E+05 | 2.2E+05 |
| | | | X | | 438.3/502.3 | 2.7E+05 | 1.1E+05 |
| Prothrombin | ETAASLLQAGYK | 0.2 | | | 626.3/879.5 | 2.8E+05 | 4.3E+04 |
| | | | X | | 626.3/679.4 | 3.9E+05 | 6.5E+04 |
| | | | | X | 630.3/887.5 | 4.4E+04 | 1.5E+05 |
| Serum albumin | LVNEVTEFAK | 9.3 | | | 575.4/937.4 | 1.6E+04 | 2.8E+07 |
| | | | X | | 575.4/694.4 | 1.1E+04 | 2.2E+07 |
| Serum amyloid P-component | VGEYSLYIGR | 1.3 | | | 578.8/1057.5 | 2.1E+04 | 1.6E+04 |
| | | | X | | 578.8/871.5 | 2.2E+04 | 2.0E+04 |
| Transferrin | EDPQTFYYAVAVVK | 0.3 | X | | 815.4/1160.6 | 2.5E+03 | 2.3E+05 |
| | | | | | 815.4/1288.7 | 8.9E+02 | 3.0E+04 |
| Transthyretin | AADDTWEPFASGK | 2.3 | | | 697.8/921.4 | 1.3E+05 | 8.4E+03 |
| | | | X | | 697.8/606.4 | 5.7E+05 | 3.7E+04 |
| Vitamin D-binding protein | THLPEVFLSK | 9.7 | X | | 585.8/819.5 | 1.6E+05 | 2.4E+04 |
| | | | | | 585.8/932.5 | 5.5E+04 | 3.9E+03 |
| Vitamin K-dependent protein C | WELDLDIK | 0.1 | | | 516.3/716.4 | 4.4E+02 | 2.3E+04 |
| | | | | | 516.3/603.3 | 3.8E+02 | 1.7E+04 |
| | | | | X | 520.3/724.4 | 3.7E+04 | 8.4E+03 |
| Vitronectin | DVWGIEGPIDAAFTR | 6.4 | | | 823.9/947.5 | 6.7E+04 | 8.1E+04 |
| | | | | | 823.9/890.5 | 3.5E+04 | 4.1E+04 |
| | FEDGVLDPDYPR | 2.2 | X | | 711.9/875.4 | 2.6E+05 | 8.5E+04 |
| | | | | | 711.9/1031.5 | 9.1E+04 | 2.7E+04 |
| Zinc-alpha-2-glycoprotein | EIPAWVPFDPAAQITK | 6.2 | X | | 891.9/1087.7 | 7.6E+03 | 3.4E+04 |
| | | | | | 891.9/728.4 | 3.8E+03 | 1.7E+04 |
| | | | | | Average values: | 3.1E+05 | 4.7E+05 |

| MRM Count | | Mean Peak Areas | | | | | | |
|---|---|---|---|---|---|---|---|---|
| Protein | Peptide Sequence | C | D | E | CV (%) | | | |
| Afamin | DADPDTFFAK | 3.2E+04 | 1.6E+05 | 3.7E+05 | | 0 | | |
| | | 3.5E+04 | 3.1E+04 | 7.0E+04 | 5 | 7 | 0 | 0 |
| Alpha-1-acid glycoprotein 1 | NWGLSVYADKPETTK | 1.9E+05 | 1.6E+05 | 3.1E+05 | 2 | | | 7 |
| | | 3.3E+05 | 3.0E+05 | 5.9E+05 | 3 | | | 6 |
| | | 6.4E+03 | 9.0E+03 | 2.5E+04 | 1 | 1 | 5 | 6 |
| Alpha-1-antichymotrypsin | EIGELYLPK | 7.5E+05 | 4.3E+05 | 9.9E+05 | | | | |
| | | 1.1E+06 | 5.7E+05 | 1.3E+06 | | | | |
| | | 5.7E+04 | 8.3E+04 | 2.0E+05 | 2 | | | |
| Alpha-1B-glycoprotein | LETPDFQLFK | 1.9E+05 | 1.2E+05 | 3.0E+05 | | 1 | | 4 |
| | | 5.0E+05 | 3.0E+05 | 8.1E+05 | | | | 1 |
| Alpha-2-antiplasmin | LGNQEPGGQTALK | 1.5E+05 | 2.2E+05 | 5.7E+05 | 0 | 0 | | |
| | | 1.4E+04 | 1.9E+04 | 4.9E+04 | 8 | 9 | 5 | 0 |
| | | 4.4E+04 | 3.1E+04 | 9.5E+05 | 0 | | | |
| Alpha-1-antitrypsin | DTEEEDFHVDQVTTVK | 3.5E+03 | 3.0E+03 | 1.8E+04 | 3 | 6 | 4 | 3 |
| | | 4.5E+03 | 6.6E+03 | 4.1E+04 | 3 | 3 | 9 | 3 |
| Alpha-2-macroglobulin | LLIYAVLPTGDVIGDSAK | 1.6E+04 | 4.2E+05 | 4.3E+05 | 0 | 9 | | |
| | | 6.2E+03 | 1.4E+05 | 1.4E+06 | 1 | 0 | | |
| Angiotensinogen | ALQDQLVLVAAK | 2.2E+03 | 1.6E+04 | 1.8E+04 | 6 | | | 3 |
| | | 3.0E+03 | 2.4E+04 | 2.3E+04 | 1 | 6 | 0 | 6 |
| | | 1.3E+05 | 4.5E+04 | 5.4E+04 | 7 | | 0 | |
| | PKDPTFIPAPIQAK | 5.0E+04 | 1.6E+04 | 2.9E+04 | 7 | | 5 | 1 |
| | | 5.7E+04 | 1.8E+04 | 3.6E+04 | 9 | | 4 | 5 |
| Antithrombin-III | DDLYVSDAFHK | 1.4E+05 | 2.6E+04 | 4.2E+04 | | 0 | 3 | |
| | | 5.1E+05 | 9.3E+04 | 1.5E+05 | | | | |
| | | 4.2E+03 | 7.7E+03 | 1.2E+04 | 1 | 5 | 2 | 7 |
| Apolipoprotein A-I | ATEHLSTLSEK | 4.3E+06 | 6.8E+05 | 1.6E+06 | | | | 2 |
| | | 3.8E+06 | 5.5E+05 | 1.3E+06 | | | | 2 |
| | | 2.9E+04 | 2.6E+04 | 6.6E+04 | | 4 | | |
| Apolipoprotein A-II precursor | SPELQAEAK | 7.7E+05 | 1.1E+06 | 2.4E+06 | 1 | | | 0 |
| | | 1.6E+06 | 2.1E+06 | 4.9E+06 | 4 | | | 1 |
| Apolipoprotein A-IV | SLAPYAQDTQEK | 1.7E+04 | 6.1E+04 | 1.6E+05 | 0 | 5 | | |
| | | 4.3E+04 | 1.3E+05 | 3.4E+05 | 6 | 1 | | |
| Apolipoprotein B-100 | FPEVDVLTK | 4.2E+05 | 1.4E+05 | 3.0E+05 | | | | |
| | | 3.8E+05 | 1.2E+05 | 2.7E+05 | | | | |
| | | 8.4E+04 | 1.3E+05 | 2.8E+05 | | | | |
| | TEVIPPLIENR | 1.0E+06 | 3.3E+05 | 8.1E+05 | 1 | | | |
| | | 2.7E+05 | 7.7E+04 | 2.0E+05 | | | 1 | 0 |
| Apolipoprotein C-I lipoprotein | TPDVSSALDK | 2.9E+04 | 2.1E+04 | 5.3E+04 | 8 | 7 | 0 | |
| | | 2.2E+04 | 1.4E+04 | 3.7E+04 | 3 | 7 | 2 | |
| Apolipoprotein C-II lipoprotein | STAAMSTYTGIFTDQVLSVLK | 6.8E+03 | 8.1E+03 | 1.7E+04 | 1 | 6 | 2 | 7 |
| | | 9.2E+03 | 5.0E+02 | 5.3E+03 | 5 | 0 | 01 | 9 |
| Apolipoprotein | DALSSVQESQVAQQAR | 1.5E+03 | 1.2E+05 | 3.6E+05 | 0 | | 1 | |

TABLE 2-continued

| Protein | Peptide | | | | | | | | |
|---|---|---|---|---|---|---|---|---|---|
| C-III | | 2.6E+04 | 2.2E+04 | 6.4E+04 | 6 | 2 | 4 | 1 | |
| Apolipoprotein E | LGPLVEQGR | 8.7E+03 | 5.7E+04 | 1.5E+05 | 0 | 7 | 6 | | |
| | | 2.0E+04 | 1.3E+05 | 3.5E+05 | | 7 | | | |
| Beta-2-glycoprotein I | ATVVYQGER | 1.6E+05 | 7.0E+05 | 1.8E+06 | | 8 | | | |
| | | 1.7E+05 | 7.0E+05 | 1.7E+06 | | 5 | | | |
| | EHSSLAFWK | 2.4E+03 | 1.9E+04 | 6.0E+04 | 0 | 6 | 7 | 6 | 9 |
| | | 3.1E+03 | 4.1E+03 | 1.8E+04 | 7 | 6 | 6 | 9 | 7 |
| | | 5.1E+03 | 4.1E+04 | 2.2E+04 | 6 | 8 | 1 | 3 | 4 |
| C4b-binding protein alpha chain | LSLEIEQLELQR | 2.3E+03 | 7.4E+04 | 5.1E+04 | 2 | 7 | 0 | 2 | 2 |
| | | 1.1E+03 | 6.5E+03 | 4.4E+04 | 6 | 1 | 5 | 6 | 1 |
| Ceruloplasmin | EYTDASFTNR | 6.4E+04 | 4.1E+05 | 1.1E+06 | | 9 | | | |
| | | 5.4E+04 | 3.5E+05 | 9.2E+05 | | 8 | | | |
| Clusterin | LFDSDPITVTVPVEVSR | 4.3E+05 | 2.4E+05 | 7.5E+05 | 9 | 3 | 9 | | |
| | | 9.1E+05 | 5.2E+05 | 1.7E+06 | 9 | 1 | 3 | | |
| Coagulation factor V | DPPSDLLLLK | 1.5E+04 | 7.3E+03 | 1.5E+04 | 8 | 6 | 0 | 9 | 7 |
| | | 2.9E+04 | 3.4E+04 | 7.7E+04 | 4 | 2 | | | |
| Coagulation factor XIIa light chain | VVGGLVALR | 1.1E+04 | 3.4E+04 | 5.6E+04 | 1 | 0 | 7 | | |
| | | 1.3E+05 | 4.1E+05 | 6.9E+05 | | | | | |
| Complement C3 | TGLQEVEVK | 5.7E+03 | 1.6E+06 | 4.0E+06 | | 5 | | | |
| | | 9.0E+03 | 1.2E+06 | 3.2E+06 | | 5 | | | |
| | | 3.5E+04 | 3.5E+04 | 1.0E+05 | 1 | 3 | 0 | 4 | |
| Complement C4 gamma chain | ITQVLHFTK | 3.1E+04 | 9.4E+04 | 8.6E+04 | | 0 | | | 2 |
| | | 3.7E+04 | 1.2E+05 | 1.0E+05 | | 8 | 2 | | |
| | | 5.8E+03 | 2.1E+04 | 2.5E+04 | 5 | 9 | | 0 | 3 |
| Complement C4 beta chain | VGDTLNLNLR | 1.0E+06 | 7.9E+05 | 1.4E+06 | | | | | |
| | | 3.6E+05 | 2.8E+05 | 4.9E+05 | | | | | |
| Complement C9 | AIEDYINEFSVR | 2.8E+04 | 2.3E+04 | 1.5E+05 | | 1 | 4 | 0 | |
| | | 1.7E+04 | 1.3E+04 | 8.5E+04 | | 0 | 4 | 0 | |
| Complement factor B | EELLPAQDIK | 2.2E+06 | 1.8E+06 | 4.6E+06 | | | | | |
| | | 3.0E+05 | 2.4E+05 | 6.1E+05 | | 1 | | | |
| Complement factor H | SPDVINGSPISQK | 1.1E+04 | 4.0E+04 | 1.1E+05 | | 2 | 4 | 0 | |
| | | 8.4E+03 | 2.6E+04 | 7.4E+04 | | 3 | 7 | | 0 |
| Fibrinogen alpha chain | TVIGPDGHK | 3.8E+15 | 1.0E+06 | 2.4E+06 | 2 | 2 | | | |
| | | 2.9E+05 | 8.5E+05 | 2.1E+06 | 1 | | | | |
| | | 5.7E+04 | 1.0E+06 | 2.4E+06 | 9 | 6 | | 0 | |
| | GSESGIFTNTK | 1.1E+05 | 7.9E+05 | 1.9E+06 | | 7 | | | |
| | | 1.1E+05 | 7.5E+05 | 1.8E+06 | | 7 | | | |
| Fibrinogen beta chain | QGFGNVATNTDGK | 4.8E+05 | 9.3E+04 | 2.5E+05 | | 6 | | | |
| | | 1.4E+05 | 2.6E+04 | 6.8E+04 | | 1 | | 2 | 0 |
| | | 1.3E+04 | 9.4E+04 | 2.9E+05 | | 6 | | | |
| Fibrinogen gamma chain | DTVQIHDITGK | 1.8E+06 | 2.2E+04 | 5.4E+04 | | | | 1 | |
| | | 1.6E+06 | 4.5E+04 | 1.1E+05 | | | | | |
| | | 2.5E+04 | 2.6E+04 | 6.6E+04 | 3 | 4 | | 7 | |
| Fibronectin | DLQFVEVTDVK | 2.4E+04 | 8.2E+04 | 2.3E+05 | | 3 | | | |
| | | 8.1E+04 | 1.1E+05 | 3.0E+05 | | | 0 | | |
| | VTWAPPPSIDLTNFLVR | 2.1E+03 | 1.6E+04 | 2.0E+04 | 1 | 7 | 4 | 4 | 1 |
| | | 2.5E+03 | 1.2E+04 | 1.6E+04 | 7 | 8 | 5 | 0 | 8 |
| Gelsolin, isoform 1 | TGAQELLR | 1.0E+04 | 1.2E+05 | 3.1E+05 | | 4 | | | |
| | | 1.5E+04 | 1.6E+05 | 4.2E+05 | | 3 | 4 | | |
| Haptoglobin beta chain | VGYVSGWGR | 4.6E+06 | 7.7E+04 | 1.9E+05 | | | | | |
| | | 2.1E+06 | 4.1E+04 | 9.4E+04 | | 1 | | | |
| Hemopexin | NFPSPVDAAFR | 6.0E+06 | 3.8E+06 | 7.0E+05 | | | | | |
| | | 4.2E+06 | 3.1E+06 | 5.9E+06 | | | | | |
| Heparin cofactor II | TLEAQLTPR | 2.0E+04 | 3.2E+05 | 8.7E+05 | | 2 | | | |
| | | 1.8E+04 | 2.5E+05 | 6.8E+05 | | 5 | | | |
| Histidine-rich glycoprotein | DSPVLIDFFEDTER | 3.1E+04 | 1.1E+05 | 1.5E+05 | 4 | 3 | 2 | | 1 |
| | | 3.2E+04 | 1.1E+05 | 1.6E+05 | 3 | 6 | 2 | 0 | 1 |
| Inter-alpha-trypsin inhibitor heavy chain | AAISGENAGLVR | 9.3E+04 | 6.3E+05 | 1.6E+06 | | 7 | | | |
| | | 2.3E+04 | 1.8E+05 | 4.6E+05 | | 4 | | | |
| Inter-alpha-trypsin inhibitor light | AFIQLWAFDAVK | 2.8E+03 | 2.9E+03 | 2.6E+03 | 3 | 1 | 2 | 0 | 9 |
| | | 7.3E+02 | 1.2E+03 | 1.1E+03 | 4 | 7 | 2 | 6 | 9 |
| Kininogen | TVGSDTFYSFK | 9.0E+05 | 6.4E+05 | 1.4E+06 | | | | | |
| | | 8.2E+04 | 5.6E+04 | 1.1E+05 | | 0 | 8 | | 5 |
| L-selectin | AEIEYLEK | 5.6E+03 | 1.7E+04 | 4.7E+04 | 6 | 5 | 9 | 4 | |
| | | 2.5E+04 | 1.3E+04 | 3.3E+04 | 7 | 2 | 5 | 2 | 1 |
| | | 1.6E+03 | 1.7E+05 | 5.0E+05 | | 4 | | | |
| Plasma retinol-binding protein precursor | YWGVASFLQK | 1.3E+04 | 4.8E+05 | 6.1E+05 | | 7 | 5 | 7 | 8 |
| | | 1.1E+04 | 2.8E+05 | 4.2E+04 | | 0 | 3 | 6 | 6 |
| Plasminogen | LSSPAVITDK | 4.7E+04 | 1.7E+05 | 4.3E+05 | | 8 | 1 | | |
| | | 3.2E+04 | 1.1E+05 | 2.7E+05 | | 3 | 1 | | |
| | | 1.0E+04 | 1.8E+05 | 5.1E+05 | | 5 | | | |
| | LFLEPTR | 1.2E+06 | 5.0E+05 | 1.2E+06 | | 8 | | | |
| | | 6.4E+05 | 2.9E+05 | 6.1E+05 | | | | | |
| Prothrombin | ETAASLLQAGYK | 1.8E+05 | 1.3E+05 | 3.1E+05 | | 0 | 0 | | |
| | | 2.3E+05 | 2.0E+05 | 5.2E+05 | | | | | |
| | | 4.4E+04 | 7.7E+04 | 2.1E+05 | 3 | | | | |
| Serum albumin | LVNEVTEFAK | 1.7E+08 | 7.7E+03 | 1.7E+04 | 4 | 9 | | 8 | 3 |
| | | 1.3E+08 | 5.8E+03 | 1.2E+04 | 4 | | | | 8 |
| Serum amyloid P-component | VGEYSLYIGR | 2.7E+04 | 1.0E+05 | 5.5E+04 | | | 7 | | 1 |
| | | 2.8E+04 | 1.2E+05 | 6.2E+04 | 1 | | 2 | | 0 |

TABLE 2-continued

| Protein | Peptide | | | | | | | | |
|---|---|---|---|---|---|---|---|---|---|
| Transferrin | EDPQTFYYAVAVVK | 1.5E+05 | 4.8E+03 | 5.2E+03 | 0 | 1 | | 1 | 4 |
| | | 2.0E+04 | 4.4E+02 | 6.5E+02 | 6 | 0 | 0 | 9 | 8 |
| Transthyretin | AADDTWEPFASGK | 2.1E+05 | 7.7E+04 | 2.0E+05 | | | 6 | | |
| | | 9.3E+05 | 3.7E+05 | 9.7E+05 | | | 4 | | |
| Vitamin D-binding protein | THLPEVFLSK | 1.5E+05 | 9.6E+04 | 2.8E+05 | | | 7 | 2 | 7 |
| | | 4.9E+04 | 3.2E+04 | 8.7E+04 | 3 | 4 | 4 | 2 | 4 |
| Vitamin K-dependent protein C | WELDLDIK | 4.8E+03 | 5.9E+03 | 3.7E+04 | 1 | 1 | 5 | 0 | 7 |
| | | 7.3E+03 | 1.2E+04 | 6.9E+04 | 8 | 1 | 0 | 7 | 3 |
| | | 3.9E+04 | 5.7E+02 | 4.8E+02 | | 2 | 2 | 4 | 2 |
| Vitronectin | DVWGIEGPIDAAFTR | 4.7E+04 | 1.4E+05 | 2.7E+05 | 6 | 7 | 6 | | |
| | | 2.6E+04 | 7.7E+04 | 1.4E+05 | 5 | 9 | 2 | | |
| | FEDGVLDPDYPR | 4.5E+05 | 1.7E+05 | 3.8E+05 | | | | | |
| | | 1.5E+05 | 5.5E+04 | 1.2E+05 | | | 4 | | |
| Zinc-alpha-2-glycoprotein | EIPAWVPFDPAAQITK | 2.0E+05 | 1.4E+04 | 2.4E+04 | 0 | 9 | 2 | 3 | 5 |
| | | 9.8E+04 | 7.3E+03 | 1.4E+04 | 3 | 8 | 7 | 2 | 9 |
| | | 2.5E+06 | 2.6E+05 | 6.0E+05 | 3 | 0 | 3 | 1 | 1 |

TABLE 3

CV using 2 fragments instead of 1

| Experiment | Avg CV sum of frags | Avg CV frag 1 | Avg CV frag 2 |
|---|---|---|---|
| A | 10.5% | 11.8% | 14.8% |
| B | 16.2% | 20.0% | 19.4% |
| C | 11.0% | 13.0% | 14.4% |
| D | 8.0% | 9.4% | 12.3% |
| E | 8.5% | 9.4% | 11.9% |

What is claimed is:

1. A mass spectrometric based assay for presence of a protein in a sample without the use of a standard for the protein, comprising the steps of:

predicting one or more of the proteolytic fragments of a protein based on one or more of an amino acid sequence for the protein and a translation of a gene sequence for the protein;

predicting one or more of the fragments produced from one or more of the proteolytic fragments of the protein when the proteolytic fragment is subjected to collision induced dissociation;

providing a sample containing proteolytic fragments of a protein;

loading at least a portion of the sample on a chromatographic column;

subjecting at least a portion of the eluent from the chromatographic column to multiple reaction monitoring, the transmitted parent ion m/z range of each multiple reaction monitoring scan including a m/z value of one or more of the predicted proteolytic fragments of the protein and the transmitted daughter ion m/z range of each multiple reaction monitoring scan including a m/z value of one or more of the predicted collision induced dissociation fragments of the predicted proteolytic fragments;

measuring the ion signal of the m/z value range encompassing one or more of the predicted collision induced dissociation fragments m/z value using said multiple reaction monitoring;

performing a substantially full product ion scan on a m/z value range encompassing a predicted proteolytic fragment m/z value when the measured ion signal corresponding to one or more collision induced dissociation fragments of the predicted proteolytic fragment is above a specified signal threshold;

measuring the ion signals associated with the parent-daughter ion transitions of said substantially full product ion scan;

selecting as the parent-daughter ion transition for an assay of the presence of the protein in a sample a parent-daughter ion transition of said substantially full product ion scan, wherein the selected parent-daughter ion transition for the assay corresponds to a transition where the transmitted parent ion is a proteolytic fragment of said protein, and wherein the selected parent-daughter ion transition has, relative to the measured ion signals associated with the other parent-daughter ion transitions for said protein, one or more of the approximately highest ion signal and the approximately highest signal-to-noise ratio; and refining the selection of the predicted collision induced dissociation fragments of the predicted proteolytic fragments based on at least one or more of the measured full product ion scans;

subjecting at least a portion of the eluent from the chromatographic column to multiple reaction monitoring, the transmitted parent ion m/z range of each multiple reaction monitoring scan including a m/z value of one or more of the refined daughter ion m/z range of each multiple reaction monitoring scan including a m/z value of one or more of the refined predicted collision induced dissociation fragments of the predicted proteolytic fragments; and measuring the ion signal of the m/z value range encompassing one or more of the refined predicted collision induced dissociation fragments m/z value using said multiple reaction monitoring.

2. The method of claim 1, wherein the sample containing proteolytic fragments of a protein is derived from at least one of a physiological fluid, a cell lysate, a tissue lysate, and combinations thereof.

3. The method of claim 2, wherein the physiological fluid comprises one or more of blood, serum, plasma, sweat, tears, urine, cerebrospinal fluid, peritoneal fluid, lymph, vaginal secretion, semen, spinal fluid, ascetic fluid, saliva, sputum, breast exudates, and combinations thereof.

4. The method of claim 2, wherein the physiological fluid comprises blood.

5. The method of claim 4, wherein the blood sample is depleted of at least six most abundant proteins before proteolytic fragmentation of the protein.

6. The method of claim 4, wherein the blood sample is plasma or serum.

7. The method of claim 4, wherein the blood sample contains the protein in a concentration of less than 100,000 attomoles/microliter.

8. The method of claim 4, wherein the blood sample contains the protein in a concentration of less than 10,000 attomoles/microliter.

9. The method of claim 4, wherein the blood sample contains the protein in a concentration of less than 1,000 attomoles/microliter.

10. The method of claim 4, wherein the blood sample contains the protein in a concentration of less than 100 attomoles/microliter.

11. The method of claim 4, wherein the blood sample contains the protein in a concentration of less than 10 attomoles/microliter.

12. The method of claim 4, wherein the blood sample contains the protein in a concentration of less than about 1 attomoles/microliter.

13. The method of claim 1, wherein the proteolytic fragments of a protein comprise tryptic peptides.

14. The method of claim 1, wherein the sample containing proteolytic fragments of a protein further comprises a concentration standard for one or more of the predicted proteolytic fragments of the protein, said concentration standard selected based on the parent-daughter ion transition selected as an assay of the presence of the protein in the biological sample.

15. The method of claim 1, wherein said step of subjecting at least a portion of the eluent from the chromatographic column to multiple reaction monitoring comprises using a triple quadrupole ion trap mass spectrometer.

16. The method of claim 15, wherein the ion trap comprises a linear trap.

17. The method of claim 1, wherein said step of measuring the ion signal of the m/z value range encompassing one or more of the predicted collision induced dissociation fragments m/z value using said multiple reaction monitoring comprises: sequencing the transmitted parent ion when the measured ion signal corresponding to one or more collision induced dissociation fragments of the predicted proteolytic fragment is above the specified signal threshold; and performing said substantially full product ion scan on a m/z value range encompassing said sequenced transmitted parent ion when the sequence of the sequenced transmitted parent ion corresponds to a proteolytic fragment of the protein.

18. The method of 17, further comprising the step of: measuring the charge state of the transmitted parent ion when the measured ion signal corresponding to one or more collision induced dissociation fragments of the predicted proteolytic fragment is above a specified signal threshold.

* * * * *